United States Patent
Venugopal et al.

(10) Patent No.: US 12,076,142 B2
(45) Date of Patent: Sep. 3, 2024

(54) PHYSIOLOGICAL MONITORING SYSTEM FOR MEASURING OXYGEN SATURATION

(71) Applicant: Apple Inc., Cupertino, CA (US)

(72) Inventors: Vivek Venugopal, Santa Clara, CA (US); Ueyn L. Block, Menlo Park, CA (US); Brian R. Land, Woodside, CA (US); Paul D. Mannheimer, Los Altos, CA (US); Albert E. Cerussi, San Jose, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 18/213,506

(22) Filed: Jun. 23, 2023

(65) Prior Publication Data
US 2023/0329597 A1    Oct. 19, 2023

Related U.S. Application Data

(62) Division of application No. 17/018,850, filed on Sep. 11, 2020, now Pat. No. 11,717,197.
(Continued)

(51) Int. Cl.
*A61B 5/1455* (2006.01)
*A61B 5/00* (2006.01)
(Continued)

(52) U.S. Cl.
CPC ........ *A61B 5/14552* (2013.01); *A61B 5/7278* (2013.01); *A61L 31/028* (2013.01);
(Continued)

(58) Field of Classification Search
CPC ... A61B 5/1455; A61B 5/1552; A61B 5/7278; A61B 5/681
See application file for complete search history.

(56) References Cited

U.S. PATENT DOCUMENTS 4,913,150 A    4/1990    Cheung et al.
6,313,612 B1   11/2001   Honda
(Continued)

FOREIGN PATENT DOCUMENTS

CN    103876726    6/2014
CN    203943664    11/2014
(Continued)

OTHER PUBLICATIONS

First Office Action issued Mar. 25, 2024 in corresponding Chinese patent application CN202080022116.9.

*Primary Examiner* — Eric F Winakur
(74) *Attorney, Agent, or Firm* — Brownstein Hyatt Farber & Schreck, LLP

(57) ABSTRACT

A wearable device is described. The wearable device includes a housing having a back cover, and an optical mask on first portions of the back cover. The back cover includes a set of windows, with a first subset of windows in the set of windows being defined by an absence of the optical mask on second portions of the back cover, and a second subset of windows in the set of windows being inset in a set of openings in the back cover. An optical barrier surrounds each window in the second subset of windows. A set of light emitters is configured to emit light through at least some of the windows in the set of windows. A set of light detectors is configured to receive light through at least some of the windows in the set of windows.

20 Claims, 14 Drawing Sheets

Related U.S. Application Data

(60) Provisional application No. 62/907,445, filed on Sep. 27, 2019.

(51) Int. Cl.
   *A61L 31/02* (2006.01)
   *H01L 31/0203* (2014.01)
   *H01L 31/0216* (2014.01)
   *H01L 31/173* (2006.01)

(52) U.S. Cl.
   CPC .... *H01L 31/0203* (2013.01); *H01L 31/02164* (2013.01); *H01L 31/173* (2013.01); *A61B 5/681* (2013.01); *A61B 2562/0242* (2013.01); *A61B 2562/04* (2013.01)

(56) References Cited

U.S. PATENT DOCUMENTS

| | | | |
|---|---|---|---|
| 6,526,300 B1 | 2/2003 | Kiani et al. |
| 6,662,033 B2 | 12/2003 | Casciani et al. |
| 6,882,874 B2 | 4/2005 | Huiku |
| 7,206,621 B2 | 4/2007 | Aoyagi et al. |
| 8,463,345 B2 | 6/2013 | Kuhn et al. |
| 8,948,832 B2 | 2/2015 | Hong et al. |
| 9,226,663 B2 | 1/2016 | Fei |
| 9,558,336 B2 | 1/2017 | Lee |
| 9,597,014 B2 | 3/2017 | Venkatraman et al. |
| 9,743,838 B2 | 8/2017 | Richards |
| 9,763,607 B1 | 9/2017 | Acosta et al. |
| 10,032,557 B1 | 7/2018 | Bossetti |
| 10,092,197 B2 | 10/2018 | Han |
| 10,117,587 B2 | 11/2018 | Han |
| 10,165,954 B2 | 1/2019 | Lee |
| 10,178,959 B1 | 1/2019 | Homyk |
| 10,181,021 B2 | 1/2019 | Verkatraman et al. |
| 10,188,330 B1 | 1/2019 | Kadlec et al. |
| 10,241,476 B1 | 3/2019 | Moten |
| 10,278,592 B2 | 5/2019 | Fish et al. |
| 10,417,513 B2 | 9/2019 | Lee |
| 10,433,739 B2 | 10/2019 | Weekly et al. |
| 10,444,067 B2 | 10/2019 | Hsu et al. |
| 10,485,437 B2 | 11/2019 | Wei et al. |
| 10,485,478 B1 | 11/2019 | Mirov |
| 10,537,270 B2 | 1/2020 | Sarussi et al. |
| 10,586,525 B1 | 2/2020 | Wu et al. |
| 10,627,783 B2 | 4/2020 | Rothkopf |
| 10,646,145 B2 | 5/2020 | Pekander et al. |
| 10,687,718 B2 | 6/2020 | Allec et al. |
| 10,702,211 B2 | 7/2020 | Clavelle et al. |
| 10,732,574 B2 | 8/2020 | Shim et al. |
| 10,736,552 B2 | 8/2020 | Ferber et al. |
| 10,760,955 B2 | 9/2020 | Chu et al. |
| 10,918,322 B2 | 2/2021 | Shao |
| 10,966,643 B1 | 5/2021 | Vavadi |
| 11,018,524 B2 | 5/2021 | Simpson |
| 11,076,769 B2 | 8/2021 | Lee |
| 11,145,310 B2 | 10/2021 | Sakurai |
| 11,224,381 B2 | 1/2022 | McHale et al. |
| 11,573,351 B2 | 2/2023 | Mehra et al. |
| 11,717,197 B2 | 8/2023 | Venugopal et al. |
| 11,723,563 B1 | 8/2023 | Shaga et al. |
| 2015/0054348 A1 | 2/2015 | Akiya |
| 2015/0099943 A1 | 4/2015 | Russell |
| 2016/0129279 A1 | 5/2016 | Ferolito |
| 2016/0278712 A1 | 9/2016 | Sagara |
| 2017/0095216 A1 | 4/2017 | Laty |
| 2017/0135633 A1 | 5/2017 | Connor |
| 2017/0172476 A1 | 6/2017 | Schilthuizen |
| 2017/0251963 A1 | 9/2017 | Hashimoto et al. |
| 2017/0315511 A1* | 11/2017 | Shim | A61B 5/1455 |
| 2017/0325698 A1* | 11/2017 | Allec | A61B 5/14552 |
| 2018/0344175 A1 | 12/2018 | Rulkov et al. |
| 2019/0072912 A1 | 3/2019 | Pandya et al. |
| 2019/0090766 A1 | 3/2019 | Block et al. |
| 2019/0090806 A1 | 3/2019 | Clavelle et al. |
| 2019/0167124 A1 | 6/2019 | Verkruijsse et al. |
| 2020/0163616 A1 | 5/2020 | Sakaya |
| 2022/0085231 A1 | 3/2022 | Liu et al. |
| 2023/0341991 A1 | 10/2023 | Shaga et al. |

FOREIGN PATENT DOCUMENTS

| | | |
|---|---|---|
| CN | 105249939 A | 1/2016 |
| CN | 109589095 | 4/2019 |
| CN | 109645972 | 4/2019 |
| CN | 110169765 A | 8/2019 |
| CN | 110236503 A | 9/2019 |
| EP | 3451117 | 3/2019 |
| KR | 20180042472 | 4/2018 |
| TW | M410888 U | 9/2011 |
| TW | 201914521 A | 4/2019 |

\* cited by examiner

PHYSIOLOGICAL MONITORING SYSTEM FOR MEASURING OXYGEN SATURATION

CROSS-REFERENCE TO RELATED APPLICATION

This application is a division of U.S. patent application Ser. No. 17/018,850, filed Sep. 11, 2020, which is a non-provisional and claims the benefit under 35 U.S.C. § 119(e) of U.S. Provisional Patent Application No. 62/907,445, filed Sep. 27, 2019, the contents of which are incorporated herein by reference as if fully disclosed herein.

FIELD

Some of the described embodiments relate generally to physiological monitoring systems for measuring oxygen saturation and, more particularly, to reflective-type devices and systems for measuring oxygen saturation. Some of the described embodiments also or alternatively relate to emitting and receiving light through a housing of a wearable device.

BACKGROUND

The use of technology in the medical profession and the general population to monitor a user's heart rate or other types of biometric information has increased with advances in sensing technology. In some examples, sensing devices (e.g., a chest strap heart rate monitor or watch) may be capable of measuring the heart rate of a person while they are exerting themselves in a physical activity such as running, and may alert the person if the heart rate varies outside of a desired range.

In some cases, sensing devices may be used for pulse oximetry, which may be an effective and quick way to monitor heart and lung function of a person. These pulse oximetry devices may be capable of evaluating the color of blood as the amount of oxygen carried by the hemoglobin may affect the color of blood. In some examples, a pulse oximetry device may be placed on a person's finger to measure the oxygenation of the person's blood. Generally, these device measurements may be reliable due to the homogeneous nature of the small tissue area over which the measurements are taken on the person.

SUMMARY

Embodiments of the systems, devices, methods, and apparatus described in the present disclosure are directed to a wearable device used for pulse oximetry. Also described are systems, devices, methods, and apparatus directed to a wearable device having a set of openings and a set of ledges bordering the set of openings. The wearable device may include a set of windows in the openings and abutting the set of ledges. The wearable device may include a photodetector which may receive light through a window of the set of windows. The ledges and material around the perimeter of the windows may serve at least partially as a barrier to undesirable light being detected by the sensors, in that the windows may be at least partially isolated from unwanted light being sensed by the sensors.

In some examples, the present disclosure describes a wearable device that may include a housing having a back cover, and an optical mask (e.g., at least one of an ink, film, coating, or surface treatment) on first portions of the back cover. The back cover may include a set of windows, with a first subset of windows in the set of windows being defined by an absence of the optical mask on second portions of the back cover, and a second subset of windows in the set of windows being inset in a set of openings in the back cover. An optical barrier may surround each window in the second subset of windows. A set of light emitters may be configured to emit light through at least some of the windows in the set of windows. A set of light detectors may be configured to receive light through at least some of the windows in the set of windows.'

In some examples, the present disclosure describes a wearable device that may include a first set of emitters configured to emit a range of red light wavelengths, a second set of emitters configured to emit a range of infrared light wavelengths, and a set of detectors. Each detector in the set of detectors may be configured to detect amounts of at least the range of red light wavelengths and the range of infrared light wavelengths. The wearable device may also include a processor configured to operate the first set of emitters and the second set of emitters; receive indicators of the amounts of at least the range of red light wavelengths and the range of infrared light wavelengths detected by the set of detectors; and determine a blood oxygenation level using at least a subset of the indicators.

In some examples, the present disclosure describes a wearable device that may include a housing, a display viewable through a front side of the housing, and a skin-facing cover on a back side of the housing. The skin-facing cover may have an interior surface, an exterior surface, and a set of ledges bordering a set of openings. The set of openings may extend through the skin-facing cover from the interior surface to the exterior surface. The wearable device may also include a set of windows disposed in the set of openings and abutting the set of ledges, and a set of photodetectors disposed within the housing and configured to receive light through the set of windows.

In some examples, the present disclosure describes a wearable device. The wearable device may include a skin-facing cover. The skin-facing cover may include an interior surface; an exterior surface; and a set of ledges bordering a set of openings, the openings extending through the interior surface and the exterior surface; a set of windows disposed in the openings and abutting the set of ledges; and a photodetector disposed to receive light through a window in the set of windows. In some examples the skin-facing cover may be optically opaque. In some examples, the set of ledges may include a stepped ledge and/or the set of ledges may include a tapered ledge. In some examples, the skin-facing cover may be optically transparent and the set of windows may be optically transparent. In some examples, one or more ledges of the set of ledges may be coated with an optically opaque material, where the optically opaque material may be optically opaque ink. In some examples, one or more edges of one or more windows of the set of windows may be coated with an optically opaque material.

In still further examples, the photodetector may be a first photodetector and the window may be a first window, and the wearable device may further include: a second photodetector disposed to receive light through a second window of the set of windows; a first light emitter disposed to emit light through a third window in the set of windows, wherein the third window is closer to the first window than the second window; and each of the first photodetector and the second photodetector are configured to receive reflections or backscatters of the light emitted by the first light emitter. In some examples, the wearable device may further include a second light emitter disposed to emit light through a fourth window in the set of windows, wherein each of the first photodetector and the second photodetector is configured to receive reflections or backscatters of the light emitted by the second light emitter. In some examples, the first light emitter may be configured to emit red light, where each window in the set of windows may be optically transparent to at least a range of red and infrared light wavelengths; and each ledge of the set of ledges extends from an edge of one of the openings and in the approximate direction of a plane parallel to the interior surface, and each opening has a smaller diameter at the interior surface than at the exterior surface. In some examples, each window of the set of windows may be circularly shaped.

In some examples, the present disclosure describes a reflective sensing device, which may include: a first emitter configured to emit a range of red light wavelengths; a second emitter configured to emit a range of infrared light wavelengths; a first detector; a second detector, wherein the first detector and the second detector are both configured to detect at least the range of red light wavelengths emitted by the first emitter and the range of infrared light wavelengths emitted by the second emitter; and a processor configured to receive indicators of amounts of the detected range of red light wavelengths and the detected range of infrared light wavelengths received from each of the first detector and the second detector, the processor further configured to determine a blood oxygenation level using at least a subset of the indicators. In some examples, the first detector may detect the red light wavelengths emitted by the first emitter on a first optical path and the second detector may detect the red light wavelengths emitted by the first emitter on a second optical path, and the first and second optical path may be different lengths. In some examples, the reflective sensing device may further include: a third emitter configured to emit a range of green light wavelengths; and a third detector configured to detect at least the emitted range of green light wavelengths from the third emitter, wherein the processor is configured to receive the detected range of green light wavelengths from at least the third detector. In some examples, the processor may be configured to sum together indicators of amounts of detected wavelength ranges from the first detector, the second detector, and the third detector. In some examples, the first emitter, the second emitter, and the third emitter may emit light sequentially. In some examples, the processor may be configured to determine the subset of received red light and infrared light used to determined blood oxygenation, based at least in part on the received green light.

In some examples, the present disclosure describes a wearable device, which may include: a back cover including a set of windows disposed about a central portion of the back cover; a set of light emitters disposed under a first subset of the set of windows included in the back cover, the set of light emitters configured to emit at least red light and infrared light; a set of photodetectors disposed under a second subset of the set of windows included in the back cover, the set of photodetectors configured to detect at least the red light and the infrared light emitted by the set of light emitters. In some examples, the set of windows may abut a set of ledges that border a set of openings that extend through the back cover. In some examples, at least a first window of the first subset of windows may be located at a different distance than a second window for the first subset of windows from the second subset of the set of windows.

In some examples, the present disclosure describes a reflective sensing device, which may include: a housing having a back cover; a set of emitters disposed within the housing and which may include: a first subset of emitters configured to emit red light through the back cover; and a second subset of emitters configured to emit infrared light through the back cover; a set of detectors disposed within the housing and configured to detect red light received through the back cover and infrared light received through the back cover; a set of optical barriers forming part of the back cover and extending through the back cover, the set of optical barriers configured to block light emitted by the set of emitters from impinging on the set of detectors before the emitted light passes through an exterior surface of the back cover.

In some examples, the reflective sensing device may further include: a processor which may be configured to determine a blood oxygenation of a user of the reflective sensing device, wherein the blood oxygenation is determined using amounts of reflected red light and reflected infrared light detected by the set of detectors. In some examples, the set of optical barriers may define optically closed walls around at least one opening of a set of openings in the back cover, where the openings extend through the back cover. In some examples, the set of optical barriers may include hollow sleeves disposed in the set of openings of the back cover of a wearable device. In some examples, at least one emitter may be positioned to emit light within an opening defined by one of the hollow sleeves. In some examples, at least one detector of the set of detectors may be positioned to receive light through an opening defined by one of the hollow sleeves and/or at least one of the hollow sleeves may have an outer perimeter wall coated with an opaque material. In some examples, the opaque material may be an opaque ink.

In still further examples, at least one of the hollow sleeves may have an inner perimeter wall coated with an opaque material. In some examples, the reflective sensing device may further include a set of windows which may be disposed in the set of openings of the back cover. In some examples, the set of windows may be optically transparent windows. In some examples, the back cover may be an optically transparent back cover. Additionally, in some examples, the set of optical barriers may reflect at least the range of red light wavelengths and may reflect at least the range of infrared light wavelengths. In some examples, the set of optical barriers may be optically opaque. In some examples, the set of optical barriers comprises black glass.

In some examples, the present disclosure describes a wearable device, which may include: a back cover having: a substrate defining part of an interior surface and an exterior surface of the wearable device; and a set of frits extending through the substrate from the interior surface to the exterior surface and defining part of the exterior surface of the back cover, wherein the frits of the set of frits have frit openings extending through the interior surface and the exterior surface; a set of windows disposed in the frit openings and defining part of the exterior surface of the back cover; and a set of photodetectors disposed to receive light through a subset of windows of the set of windows. In some examples, the subset of windows may be a first subset of windows; and the set of windows may further include a second subset of windows of the set of windows; and the wearable device may further include a set of emitters configured to emit light through the second subset of windows. In some examples, the back cover and the set of windows may be optically transparent. In some examples, at least one window of the set of windows has an outer diameter wall coated with an optically opaque material.

In some examples, the present disclosure describes a method of forming an optical barrier in a reflective sensing device, which may include: inserting a hollow cylinder into a back cover opening of a wearable device, wherein the hollow cylinder has a centrally located opening; fusing the hollow cylinder to the back cover to form a mechanical bond between materials of the hollow cylinder and the back cover; inserting an optically transparent window into the centrally located opening of the hollow cylinder; and fusing the optically transparent window and the hollow cylinder together to form a mechanical bond between materials of the hollow cylinder and the optically transparent window, where: the hollow cylinder may be an optically opaque material and which may form an optical barrier between light emitted by an emitter configured to emit light through the back cover and a detector which may be configured to receive light through the back cover and positioned on a same side of the back cover as the emitter. In some examples, the optically opaque material comprises black glass. In some examples, each of the back cover and the windows may be sapphire.

In some examples, the present disclosure describes a reflective sensing device, which may include: a housing; a first set of emitters which may be configured to emit infrared light through the housing; a second set of emitters which may be configured to emit red light through the housing; a first set of waveguides which may be configured to guide infrared light emitted by the first set of emitters toward the housing; a second set of waveguides which may be configured to guide red light emitted by the second set of emitters toward the housing; a set of detectors which may be configured to detect reflections or backscatters of the infrared light emitted by the first set of emitters and the red light emitted by the second set of emitters; and a processor which may be configured to determine a blood oxygenation of a user of the reflective sensing device, wherein the blood oxygenation is determined using amounts of reflected or backscattered red light and reflected or backscattered infrared light detected by the set of detectors. In some examples, the first set of waveguides may be internally reflective of infrared light and/or the second set of waveguides may be internally reflective of red light. In some examples, the first set of waveguides and the second set of waveguides may be solid material and/or the core of the solid material may be internally reflective of infrared light and red light.

In some examples, the reflective sensing device may further include: a set of windows, where the set of windows may include: four emitter windows which may be configured to allow infrared light and red light emitted by the first set of emitters and the second set of emitters to pass through the emitter windows; and four detector windows which may be configured to allow reflected infrared light and reflected red light to pass through the four detector windows and to the set of detectors. In some examples, the reflective sensing device may further include: a third set of emitters which may be configured to emit green light; a third set of waveguides which may be configured to guide green light to a third set of windows of the set of windows; and the set of detectors further which may be configured to detect reflected or backscattered green light emitted by the third set of emitters.

In some examples, the present disclosure describes a wearable device, which may include: a back cover; a set of emitters which may be configured to emit light; a first set of waveguides optically coupled to the set of emitters and which may be configured to guide the emitted light through the back cover; and a photodetector of a set of photodetectors disposed to receive reflected or backscattered light emitted by the set of emitters. In some examples, at least a first waveguide of the first set of waveguides may be configured to guide light from a first set of emitters of the set of emitters, where the first set of emitters may be configured to emit red light. In some examples, at least a second waveguide of the first set of waveguides may be configured to guide light from a second set of emitters of the set of emitters, where the second set of emitters may be configured to emit infrared light.

In still further examples, the wearable device may further include: a second set of waveguides which may be configured to receive reflected red light and reflected infrared light. In some examples, the second set of waveguides may be configured to guide light to the set of detectors. In some examples, the first set of waveguides and the second set of waveguides may be hardened glass. In some examples, the second set of waveguides may be internally reflective of infrared light and red light. In some examples, the first set of waveguides may be internally reflective of red light and may be internally reflective of infrared light. In some examples, the wearable device may further include: a third set of emitters of the set of emitters, the third set of emitters which may be configured to emit green light, where the first set of waveguides and the second set of waveguides may be internally reflective of green light. In some examples, the first and second set of waveguides may be fiber optic waveguides.

In some examples, the present disclosure describes a reflective sensing device, which may include: a first emitter may be configured to emit a range of red light wavelengths; a second emitter may be configured to emit a range of infrared light wavelengths; a first detector; a second detector, where the first detector and the second detector may be both configured to detect at least the reflected range of red light wavelengths from the first emitter and on a first optical path, and the first detector and the second detector may be both configured to detect at least the reflected range of infrared light wavelengths from the second emitter and on a second optical path, where the first optical path and the second optical path may be different lengths. In some examples, the reflective sensing device may further include: a first waveguide which may be configured to guide emitted red light wavelengths; and a second waveguide which may be configured to guide emitted infrared light wavelengths. In some examples, the detected range of red light and infrared light wavelengths may be detected on a first and second optical path of different lengths which may provide a mapping of arterial or venous blood flow for pulse oximetry.

In addition to the exemplary aspects and embodiments described above, further aspects and embodiments will become apparent by reference to the drawings and by study of the following description.

BRIEF DESCRIPTION OF THE DRAWINGS

The disclosure will be readily understood by the following detailed description in conjunction with the accompanying drawings, wherein like reference numerals designate like structural elements, and in which.

Figure 1A:
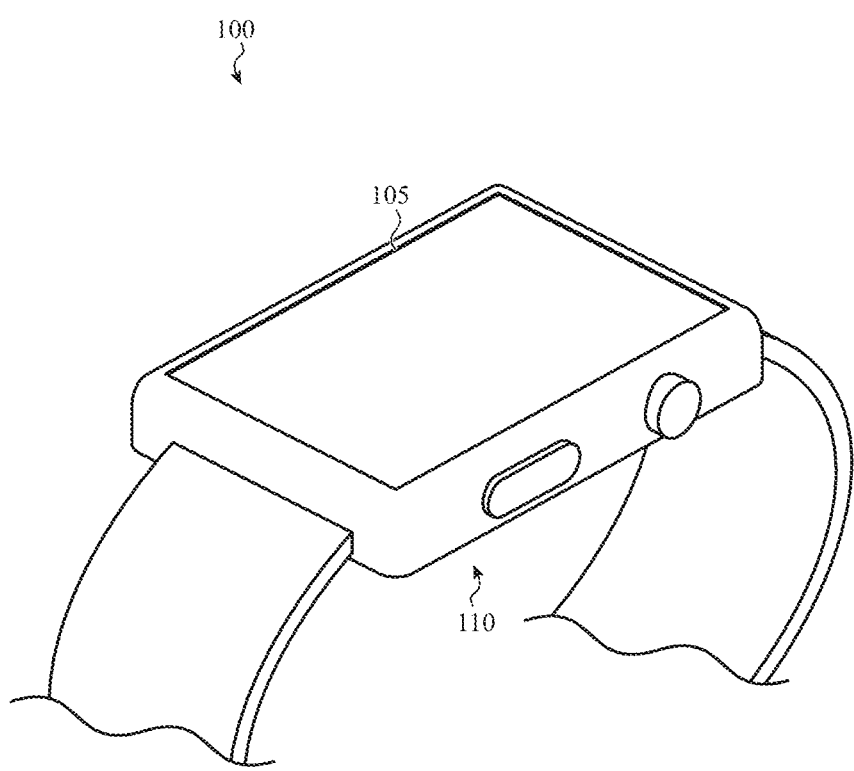
FIG. 1A illustrates an example of a wearable device.

The use of cross-hatching or shading in the accompanying figures is generally provided to clarify the boundaries between adjacent elements and also to facilitate legibility of the figures. Accordingly, neither the presence nor the absence of cross-hatching or shading conveys or indicates any preference or requirement for particular materials, material properties, element proportions, element dimensions, commonalities of similarly illustrated elements, or any other characteristic, attribute, or property for any element illustrated in the accompanying figures.

Additionally, it should be understood that the proportions and dimensions (either relative or absolute) of the various features and elements (and collections and groupings thereof) and the boundaries, separations, and positional relationships presented between them, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following description is not intended to limit the embodiments to one preferred embodiment. To the contrary, it is intended to cover alternatives, modifications, and equivalents as can be included within the spirit and scope of the described embodiments as defined by the appended claims.

Generally, different types of biometric information may be monitored on a person, such as heart rate and/or blood oxygenation. The biometric information may be monitored using sensing devices that forego the need for performing invasive procedures on the person. This information may be monitored using sensing devices such as thermometers which may be placed in the ear or on the forehead of the person, or a heart rate and/or blood oxygenation device which may be placed on the index finger of the person. One characteristic of these devices is that they are pass-through measurement type devices. When employing these devices light may be emitted into one side of the finger or ear lobe and the light may be detected on the other side of the finger or ear lobe. The light may generally pass through approximately 0.5-1.0 cm of tissue before being detected. These sensing devices may be effective for use in a controlled environment, for example, during a medical examination. To measure the blood oxygenation of a person, a sensing device such as a pulse oximeter may be placed on the index finger of the person. The pulse oximeter may measure changes in the color of blood in a small tissue area, and accordingly may use a single emitter and single detector. Further, due to the small tissue area being measured, the tissue in the small area such as an index finger or ear lobe may be relatively homogenous, which may make the measurements reasonably reliable. The index finger or ear lobe may be confined areas and well-perfused tissue areas, which may additionally make the measurements reasonably reliable. Further, finger tips are well-vascularized and generally provide strong pulsatile light signals for pulse oximetry, which may also contribute to reasonably reliable measurements. Although these technologies may provide accurate measurements, these devices are not conducive to performing measurements while a user is moving or going about their daily routine. Accordingly, sensing devices such as heart rate monitors are being integrated into wearable devices so that a person may monitor biometric data such as heart rate on a daily basis and while engaging in various activities.

Some heart rate monitors are being incorporated in chest straps, watches, and other types of fitness bands that people may wear to monitor biometric data while performing daily activities, or to monitor and/or maximize performance while exercising, training, and/or racing. Also, in the case of a device worn on a wrist or strapped to a user's chest or forehead or elsewhere, the tissue depth or structures within the tissue may significantly limit the amount of light that passes through and exits the tissue. Sensors, such as heart rate monitors or pulse oximeters, may therefore be configured as reflective-type devices that emit light into one side of a wrist or limb and receive reflection of the light through the same side of the wrist or limb. Additionally, in the case of a device attached to a user via a band, it may be useful to implement a biometric sensor system as a reflective-type sensor to avoid having to incorporate part of the sensor system into the device's band (as might be required if the sensor system were implemented as a pass-through or transmissive type sensor system). Because these sensing devices may be integrated into devices such as wrist bands, watches, and smart watches, different challenges may arise due to the heterogeneous nature of the tissue in a person's wrist. For example, wrist tissue may include a dense network of blood vessels, tendons, ligaments, and bones all or some of which may reflect, scatter, and/or absorb light, thus making measurements at the wrist challenging.

Alternatively and as discussed herein, measurements may be implemented in an improved manner, thus improving the accuracy and reliability of the measurements. In some examples, the sensing device may be a wearable device such as a watch or smart watch which may be worn on the wrist of a person. The watch may include multiple emitters and multiple detectors to image and/or optically probe the wrist tissue, which may address the heterogeneous nature of the wrist tissue and provide accurate measurements by collecting light passing through multiple regions. Further, the watch may include multiple emitters and multiple detectors to sample light that has passed through multiple tissue regions, which may address the reduced vascular density and heterogeneous nature of the wrist tissue. By employing multiple emitters and detectors, different length light paths may propagate through the tissues and may ensure that light is traveling through tissue as opposed to simply reflecting off of the tissue surface. In some less desirable cases, light may reflect off of the tissue surface if the band which may secure the device to the user is not tight, tilted, or intentionally worn loosely. The multiple emitters and multiple detectors may provide sufficient data so that a processor may be able to identify false readings and ineffective or useless measurements from the data. In some examples, the signals from the detectors (e.g., indicators of amounts of detected light) may be summed prior to processing, and in some cases regions suspected of corrupted data may be excluded. Corrupted data may be due to crosstalk due to the watch lifting off of the user's skin and/or undue tissue heterogeneity.

In order for the light from the emitters to reach the wrist tissue of the person, windows may be provided in the internal or skin-facing side of the wearable device. The windows may also provide an aperture through which reflected and/or backscattered light from the wrist tissue may be detected by the detectors. The windows may be anchored in the back cover and may be a feature through which one or more wavelengths of electromagnetic radiation may propagate. Further, the windows may be disposed in openings that extend through the back cover and in some examples, the windows may be sapphire windows. These windows may be anchored in the skin-facing side of the wearable device in various ways which will be discussed in further detail herein, and in some cases may be mounted in or on a back cover which is also formed of sapphire. Further, the methods for securing the windows in the back cover of the wearable device may also include optical isolation methods to reduce and/or eliminate internal crosstalk between the emitters and detectors.

In some examples, the light may be emitted to reach the wrist tissue of the user via a waveguide. The waveguide may guide the emitted light through the skin-facing cover or back cover and to the wrist tissue. Similarly, the reflected light may be received or detected via a waveguide which may guide the reflected light to the one or more detectors. The waveguides may guide the light and/or receive the reflected light through windows which may be anchored in the back cover. Alternatively, the waveguides may guide the light and/or receive the reflected light directly through the back cover via openings in the back cover, where no windows may be present in the back cover. The openings in the back cover may extend through the internal surface and the external surface of the back cover.

Described herein are various configurations for maximizing the use of the emitters and detectors to perform pulse oximetry. In some embodiments, the windows may be secured by employing methods that provide an optical barrier between the emitters and the detectors.

These and other embodiments are discussed below with reference to FIGS. 1A-10. However, those skilled in the art will readily appreciate that the detailed description given herein with respect to these Figures is for explanatory purposes only and should not be construed as limiting.

Directional terminology, such as "top", "bottom", "upper", "lower", "above", "below", "beneath", "front", "back", "over", "under", "left", "right", etc. is used with reference to the orientation of some of the components in some of the figures described below. Because components in various embodiments can be positioned in a number of different orientations, directional terminology is used for purposes of illustration only and is in no way limiting. The directional terminology is intended to be construed broadly, and therefore should not be interpreted to preclude components being oriented in different ways.

FIG. 1A illustrates an example of a wearable device 100. In some examples, the wearable device 100 may be configured to perform a number of biometric or physiological measurements of a user or person that may be wearing the wearable device 100. In the example of FIG. 1A, the wearable device 100 may include a reflective sensing device configured to perform pulse oximetry on the user wearing the wearable device 100.

FIG. 1A depicts one example of a wearable device 100, which may be worn on a wrist of a user and may be any type of watch, for example, a smart watch or a sport watch, or any type of biometric device, for example, a heart rate monitor, with a front side 105 and a back side 110. The back side 110 of the wearable device 100 will be discussed in further detail herein. In alternative embodiments, the wearable device may be configured to be worn on an arm, head, neck, thigh, torso, or other body part.

A user of the wearable device 100 may view a display of the wearable device 100 through the front side 105 of the wearable device 100. The display may be configured to display information such as the time, date, weather, and so forth. The display may also be configured to display biometric measurements or data (e.g., the user's heart rate or blood oxygenation) acquired by the reflective sensing device, which reflective sensing device may be at least partially visible on the back side 110 of the wearable device 100. The back side 110 of the wearable device 100 may be the skin-facing side, which may be adjacent to the skin of the user wearing the wearable device 100. In some examples, the back side 110 of the wearable device may or may not be in direct contact with the skin of the user wearing the wearable device 100. The back side 110 will be discussed in further detail herein.

In some examples, the wearable device 100 may be a watch and a biometric device. The wearable device 100 may be configured to measure various biometric user data of the user wearing the wearable device 100 such as heart rate and blood oxygenation. Because the wearable device 100 may be worn on the wrist of the user, different factors may be taken into account than other types of biometric sensors or detectors.

Biometric sensor design may consider various factors such as whether to use optical or electrical sensors, ease of use, the environment in which the sensor may be used, battery and/or power consumption, accuracy of the measurements, wavelength of the emitter, size and form factor of the detector or sensor, any combination thereof, and so forth. The terms detector and sensor may be used interchangeably herein. Some biometric sensors may measure heart rate via a chest strap which may include two electrodes. The electrodes on the chest strap may contact the skin to measure the heart rate of the user. Electrical sensors may be used for chest straps due to the dynamic movement of the user and the various environments and body conditions in which the chest strap may be used, for example, extremely cold weather, very hot weather, sweat, salt water, chlorinated water, and so forth. Although the chest strap may be bulky, may be an extra element the user has to wear, and may have a limited battery life, the ability to perform accurate measurements in multiple environments while performing dynamic movement may outweigh the inconvenience of wearing the chest strap.

Other biometric sensors utilized by medical professionals may be used and/or worn on a finger of the user, or in some cases used on the ear or ear lobe of the user. Biometric sensors such as thermometers and pulse oximeters may be configured for use in small physical areas such as on an index finger and in or on ears, which are physical body locations with blood vessels such as veins, arteries, and capillaries close to the skin surface. The proximity of the blood vessels to the skin surface in the finger may facilitate accurate measurements when detecting a heart rate or blood oxygen level. Additionally, due to the small tissue area of use on a fingertip or in an ear, these biometric sensors may be useful for controlled environments, but not as useful when performing daily routine activities. Further, the small area of a fingertip or an earlobe may provide homogenous tissue for the sensor, thus allowing accurate data to be measured when taken in the small area.

Pulse oximeters may be capable of measuring the color of a person's blood and generally provide a quick and accurate way to monitor the heart and/or lung function of a person. As the oxygen level in a person's blood varies, the color of the person's blood may change. The pulse oximeter may detect or sense that change in color of the person's blood as it varies. Because the pulse oximeters used on finger tips or ears measure a small area, the sensing devices may use a single source or emitter for each corresponding wavelength and a single detector. For example, these pulse oximeters may use a source that emits red light and a source that emits infrared light and may sense the emitted light using a single detector capable of sensing both red and infrared light.

In FIG. 1A, the wearable device 100 may be worn on the user's wrist and because pulse oximetry is being performed via the wearable device 100 with emitters and detectors on the wrist, the measurements may become more complicated. Generally, wrist tissue is heterogeneous in the area where a watch is typically worn on the wrist and may have different vascular density than a fingertip or an earlobe or ear. The wrist may have bone, tendon, veins, and arteries from which the light from the sensor may be reflected, which may provide unpredictable results, and in some cases false measurements. Additionally, the wrist area over which the measurements may be taken is a larger area than a fingertip or an ear lobe, thus making providing more data, some of which may not be accurate data.

Figure 1B:
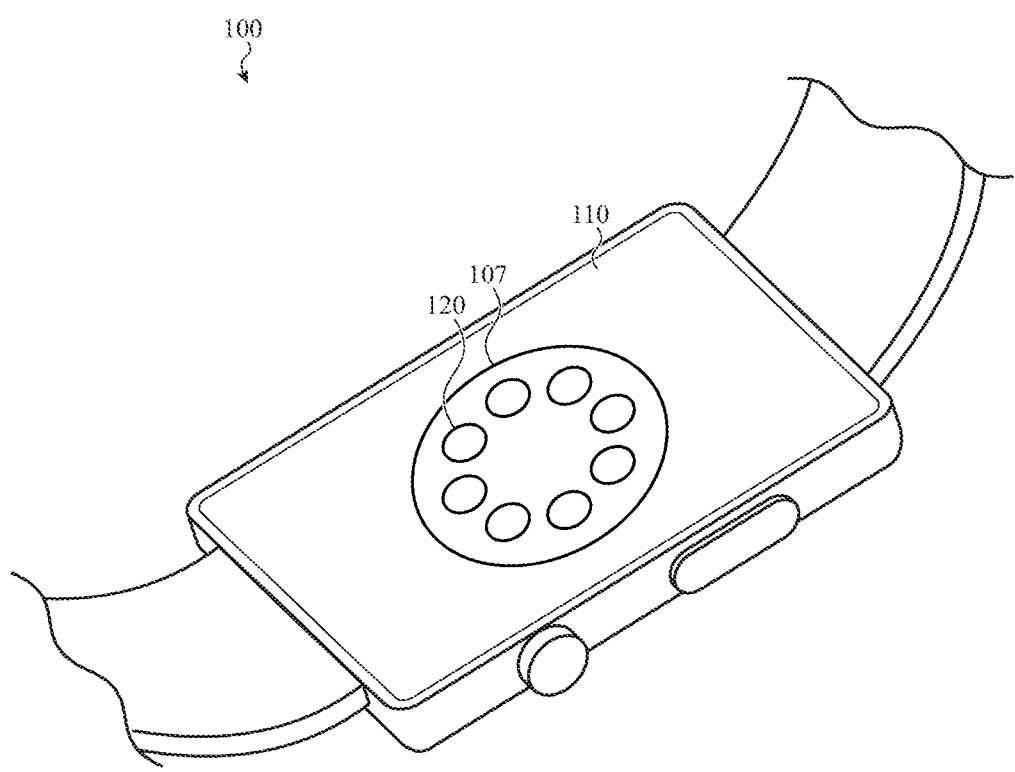
FIG. 1B illustrates an example of a wearable device.

FIG. 1B illustrates an example of a wearable device 100. Similar to FIG. 1A, the wearable device 100 may include a reflective sensing device configured to perform pulse oximetry on the user wearing the wearable device 100. FIG. 1B depicts one example of the back side 110 of the wearable device 100 shown in FIG. 1A. In some examples, the wearable device 100 of FIG. 1B may be worn on a wrist of a user and may be any type of watch, for example, a smart watch or a sport watch, or any type of biometric device, for example, a heart rate monitor, with a front side 105 (as illustrated in FIG. 1A) and a back side 110.

In FIG. 1B, the wearable device 100 includes a back cover 107 or skin-facing cover that forms part of a housing of the wearable device 100. The wearable device 100 also includes windows 120 in the back cover 107, which in some examples may be visible on the exterior surface of the skin-facing side of the wearable device 100. The back cover 107 and/or windows 120 may be formed of sapphire, glass, plastic, or other materials. In some embodiments, some or all of the windows 120 may be sapphire windows that are mounted within (i.e., inset in) openings in a sapphire back cover 107. Some or all of the windows may also be integral with the back cover 107 and defined by an absence of an optical mask (e.g., an ink (an optically opaque ink), film, coating, or surface treatment) on other portions of the back cover 107. For example, the optical mask may be on first portions (e.g., non-window portions) of the back cover 107, and absent from second portions of the back cover 107. Some of the windows 120 may provide an aperture through which the emitters of a reflective sensor system (not shown in FIG. 1B) may emit light. The emitted light may pass into the tissue of the user and then may scatter, be absorbed, or reflect off of the tendons, bones, and blood vessels of the user. The reflected light from the arterial blood may be detected by the detectors of a reflective sensor system (not shown in FIG. 1B) incorporated into the wearable device 100. Some of the windows 120 may provide an aperture through which the detectors (i.e., light detectors or photodetectors) may detect the reflected light from the tissue. The windows 120 may provide for good coupling between the windows 120 and the skin, which may ensure acceptable measurement accuracy. Further, the windows 120 may provide for optical isolation of the reflected light and methods of providing the optical isolation are discussed in further detail herein. In some embodiments, windows 120 over the emitters may be integral with the back cover 107 and windows 120 over the detectors may be inset within the back cover 107.

In some examples, the exterior surface of the back side 110 of the wearable device 100 may be in close contact with the wrist of the user which may reduce air gaps between the windows 120 and the tissue of the user. Air gaps may reduce the accuracy of the detectors as some of the light reflected from the tissue may pass through air and some of the reflected light may not due to a tilt in the wearable device 100 which makes contact to the skin in some places but not in others, thus altering the optical path to the detector and possibly affecting the detector reading. Alternatively, the wearable device 100 may be in close contact to the tissue of the user and may be too tight, thus restricting blood flow of the user and affecting the detector readings. As discussed herein, multiple emitters and multiple detectors may be used to provide the blood oxygenation measurements. In using more than one emitter and detector, there may be multiple different optical path lengths and optical path directions between the emitters and detectors. These multiple optical path lengths and optical path directions may be used to compensate for the air gaps and such by selecting the appropriate path or paths which may provide meaningful information for use in determining blood oxygenation.

Figure 2:
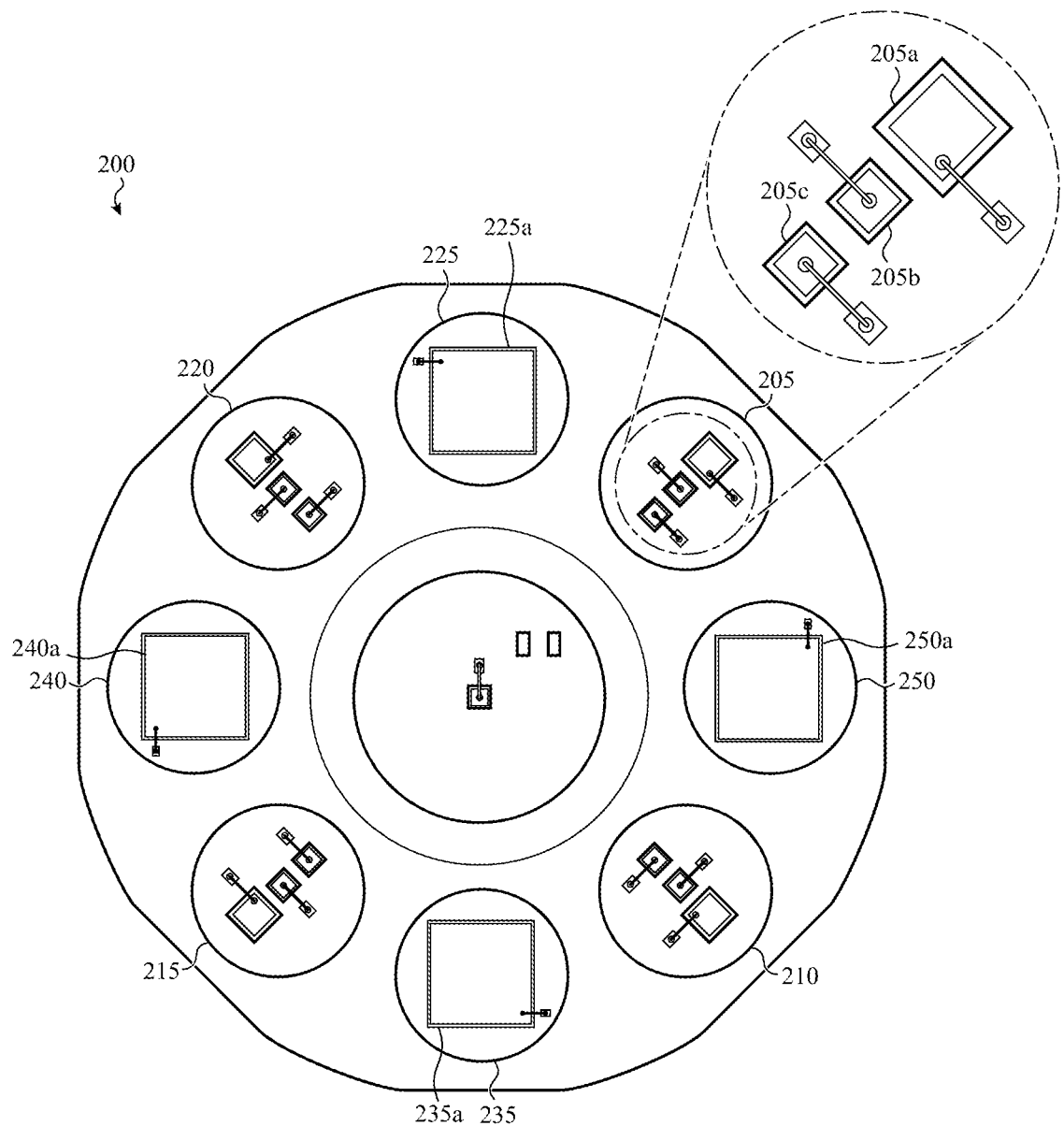
FIG. 2 illustrates an example layout of emitters and detectors.

FIG. 2 illustrates an example layout 200 of emitters and detectors. In some examples, the layout 200 of emitters and detectors may be incorporated into some aspects of the wearable device 100 as described with reference to FIGS. 1A and 1B. In the example of FIG. 2, the layout 200 of emitters and detectors may be included in the wearable device to provide physiological and/or biometric measurements of the user wearing the wearable device 100 of FIGS. 1A and 1B.

By way of example and for purposes of description, the layout 200 of emitters and detectors may be located on the skin-facing side of the wearable device 100 as discussed with reference to FIGS. 1A and 1B. The layout 200 of emitters and detectors may be protected by a back or skin-facing cover (not shown in FIG. 2) with windows or apertures which is discussed in further detail herein.

As illustrated in FIG. 2, the layout 200 may include emitters positioned within various emitter windows 205, 210, 215, and 220 (e.g., emitters 205a-c positioned within emitter window 205). FIG. 2 also shows detector 225a, detector 235a, detector 240a, and detector 250a. Emitters 205a-c may include a green light emitter 205a, an infrared light emitter 205b, and a red light emitter 205c. Similarly, each set of emitters positioned within the other emitter windows 210, 215, and 220 may include a green light emitter, an infrared light emitter, and a red light emitter. Although green light, infrared light and red light may be described as being emitted by the emitters herein, the green light may be understood to be electromagnetic radiation in the approximate range of green light wavelengths, the infrared light may be electromagnetic radiation in the approximate range of infrared light wavelengths, and the red light may be electromagnetic radiation in the approximate range of red light wavelengths. In some examples, the emitters may be a coherent light source such as a laser and/or laser diode, semi-coherent light source such as a light emitting diode or superluminescent diode, a non-coherent light source, or any other appropriate light emitting source. Additionally depicted in FIG. 2, each of the individual emitters and detectors (or photodetectors) may receive power and/or signaling via bond wires.

The detectors 225a, 235a, 240a, and 250a of windows 225, 235, 240, and 250 of FIG. 2 may be electromagnetic radiation detectors. The terms detectors and sensors may be used interchangeably herein. Each of the detectors in FIG. 2 may be configured to receive any of the emitted light from any of the emitters in emitter windows 205, 210, 215, and/or 220. The detectors 225a, 235a, 240a, and 250a may be configured to detect or receive light or photons and to convert the detected light/photons into an electrical current and/or electrical signal. Depending on the location of the emitter from which the detector receives the light, the detected light may have varying intensities due to various light scattering, absorption, and/or reflections by the wrist tissue and may be more or less easily detected by the detectors.

The detectors 225a, 235a, 240a, and 250a may detect any of the emitted green light, infrared light and/or red light emitted by the emitters in FIG. 2. Though the detectors 225a, 235a, 240a, and 250a may be described as detecting green light, infrared light, and red light, detecting the green light may be understood as detecting electromagnetic radiation in the approximate range of green light wavelengths, detecting the infrared light may be understood as detecting electromagnetic radiation in the approximate range of infrared light wavelengths, and detecting the red light may be understood as detecting electromagnetic radiation in the approximate range of red light wavelengths. In some examples, the detectors 225a of FIG. 2 may be a photodiode, a photoconductor, or any other appropriate detector capable of sensing light at the appropriate wavelengths and intensities as described herein. As discussed herein, the detectors are described as receiving or detecting light emitted from the emitters, but it may be understood that the received or detected light is reflected light and/or backscattered from the tissue. Further, the reflected and/or backscattered light may include the emitted light that has passed through the tissue, light that has reflected off the tissue surface, or both. In some examples, the detectors may be at least partially optically isolated such that the detection of light directly from emitters is at least partially reduced or minimized, and in some examples, prevented. Optically isolating the detectors is discussed in further detail herein.

The emitters 205a-205c of emitter windows 205, 210, 215, and 220 and the detectors 225a, 235a, 240a, and 250a in the layout 200 of FIG. 2, may be disposed in a ring about the central portion of the back or skin-facing cover of the wearable device or watch. As illustrated in the example of FIG. 2, the emitters 205a-205c of emitter windows 205, 210, 215, and 220 may be arranged to alternate with the detectors 225a, 235a, 240a, and 250a. That is, emitter window 205 may be adjacent to detector window 225 and detector window 250, emitter window 210 may be adjacent to detector window 235 and detector window 250, and so forth. In some examples, due to the heterogeneous nature of the tissue in the wrist, the distance between the emitters and the detectors may be maximized by arranging the emitters and detectors in a ring or ring-like shape, to image and/or encompass as much of the wrist tissue as possible for any given watch size. In some examples, the configuration of emitters and detectors may be any other shape. Windows in a skin-facing cover disposed over the emitters and detectors may also be arranged in a ring and, in some cases, windows that are integral with the skin-facing cover may be interspersed with windows that are inset in the skin-facing cover (i.e., the different types of windows may be interspersed around the ring). In the example of FIG. 2, by surrounding a central region with emitters and detectors in a ring shape may increase the coverage area with fewer components. Due to the complexity of imaging and/or optically probing heterogeneous tissue, other factors may be considered for emitter and detector layouts, in addition to maximizing the distance between the emitters and detectors, such as false readings, emitter light clipping, path or channel lengths, battery life, power consumption, any combination thereof, and so forth. These factors are discussed in further detail herein.

As illustrated in FIG. 2, the layout 200 may be configured to accommodate eight windows, which may include four emitters and four detectors for measuring pulse oximetry. Although four emitters and four detectors may be discussed herein, in some examples, six windows, which may include three emitters and three detectors, may be used to accommodate the size of the watch. Any appropriate number of multiple emitters and multiple detectors may be used for pulse oximetry so long as the configuration and number of the emitters and detectors may be integrated into the wearable device. In some examples, using four emitters and four detectors may create sixteen channels or paths between emitters and detectors or may create up to sixteen different paths between emitters and detectors. Further, as the number of emitters and detectors increases, the less sensitive the pulse oximeter measurements may be to false and/or useless readings. Although an equal number of emitters and detectors are described herein, any number of emitters and detectors may be used, including an unequal number of emitters and detectors.

Each of the windows of FIG. 2 may include a green light emitter, an infrared light emitter, and a red light emitter. For example, the emitters may include a green light emitter 205a, an infrared light emitter 205b, and a red light emitter 205c. The other green, infrared, and red light emitters of FIG. 2 may be similarly numbered. In some examples, the green light emitter may be used to measure or monitor the heart rate of the user. Additionally, the green light emitter may be located on the outside diameter and the farthest away from the central portion (or center) of the wearable device. The green light emitter may be positioned on the outer diameter because the green light may be detected by either one or both of the two closest or adjacent detectors. Due to this localized sensing of the green light in this example, the distance between, for example the green light emitter 205*a* and the detectors 235*a* and 240*a* may not be relevant as the detectors 225*a* and 250*a* are the two detectors which may sense green light emitted from the green light emitter 205*a*. In some examples, it may be possible that the detectors 235*a* and 240*a* may detect green light emitted by the green light emitter 205*a*.

The infrared light emitters and the red light emitters may be detected by any or all of the detectors 225*a*, 235*a*, 240*a*, and 250*a*, regardless of how close or far the detector may be from the emitter. In some examples, the red light emitter may be positioned closer to the central portion (or center) of the wearable device than the infrared light emitter. The red light emitter may be located closer to the middle of the wearable device because generally, the red light may be absorbed more than the infrared light, thus the red light is more sensitive to clipping than the infrared light.

In FIG. 2, the emitting area of each of the emitters 205*a-c* of emitter windows 205, 210, 215, and 225 is depicted as square, but may be any appropriate shape that allows a suitable amount of light to be emitted by the emitter. Similarly, the detecting area of the detectors 225*a*, 235*a*, 240*a*, and/or 250*a* is represented as square, but may be another shape or configuration that allows a suitable amount of light to be detected by the detector. Further, the individual emitters (e.g., light emitting diodes (LEDs)) which are depicted as square in FIG. 2 may be positioned within round apertures and the individual detectors which are depicted as square may also be positioned within round apertures. The emitters and detectors are also depicted as being approximately equidistant from one another, but may be located equidistant from one another, or may be located various distances from one another as appropriate. Additionally, should the distance between the emitters and detectors vary, the detecting angle between emitters and detectors may also vary from the layout 200 depicted in FIG. 2. The distance between the emitters and the detectors may be chosen to optimize battery life and power savings. In some examples, some of the emitters and detectors may be located closer together depending on the absorption and reflection properties of the wavelength of light. The shapes of the emitters and detectors and layout configurations are discussed in further detail herein.

In some examples of FIG. 2, the wearable device may include windows 205, 210, 215, and 220 or apertures through which the emitted light from the emitters may pass. Similarly, the windows 225, 235, 240, and 250 may also serve as an aperture through which light reflected and/or backscattered from the wrist tissue may pass back into the wearable device and be detected by the detectors. The windows 205, 210, 215, and 220 may be seated in a back cover of the wearable device. The back cover or skin-facing cover may be part of the exterior surface of the skin-facing side of the wearable device as discussed with respect to FIGS. 1A and 1B. In some examples, the windows may provide optical isolation for the detectors so that the detectors do not receive light directly from the emitters. The optical isolation via the windows and the back cover is discussed in further detail herein.

Although the windows 205, 210, 215, 220, 225, 235, 240, and 250 are circular in FIG. 2, this is for explanatory purposes and the windows may be any appropriate shape as discussed in further detail herein. Additionally, the windows are approximately the same size in FIG. 2 for explanatory purposes, but the windows may be the same size or may vary in size as appropriate.

Figure 3:
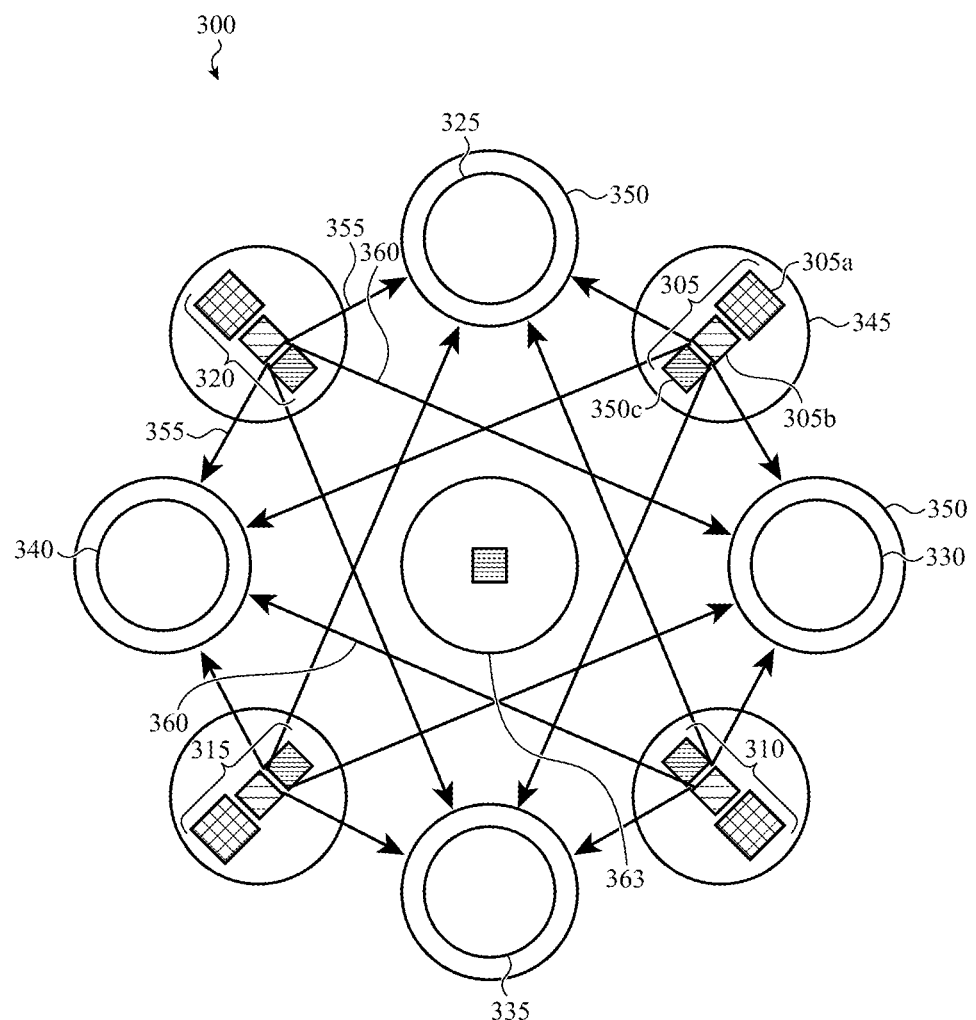
FIG. 3 illustrates an example layout of emitters and detectors.

FIG. 3 illustrates an example layout 300 of emitters and detectors. In some examples, the layout 300 of emitters and detectors may be incorporated into some aspects of the wearable device 100 as described with reference to FIGS. 1A-2. In the example of FIG. 3, the layout 300 of emitters and detectors may be included in the wearable device to provide physiological and/or biometric measurements of the user wearing the wearable device 100 of FIGS. 1A and 1B.

By way of example and for purposes of description, the layout 300 of emitters and detectors may be located on the back or skin-facing side of the wearable device 100 as discussed with reference to FIGS. 1A and 1B. The layout 300 of emitters and detectors may be protected by a back or skin-facing cover with windows or apertures (not shown in FIG. 3) which is discussed in further detail herein.

As illustrated in FIG. 3, windows 345 may include emitters 305*a*, 305*b*, and 305*c*. Similar to FIG. 2, each of the emitter windows may include the green light emitter, the infrared light emitter, and the red light emitter. For example, emitter 305 may include green light emitter 305*a*, infrared light emitter 305*b*, and red light emitter 305*c*. Additionally, in FIG. 3, the windows 350 may include detectors 325, 330, 335, and 340. Window 363 may be a window in the central portion of the back cover. The windows, emitters, and detectors, may each incorporate features of similar elements described in other embodiments.

Between each of the emitter windows 345 and detector windows 350 are multiple paths including short paths 355 and long paths 360 (i.e., for each emitter (or each detector), there are at least first and second optical paths (or light detection paths) having respective first and second lengths). Further, methods of mounting or inserting the detector windows 350 into the back cover may provide optical isolation such that stray light from the emitters will not be detected by the detectors. In some examples, the windows alone may not provide sufficient light blocking from the internal crosstalk of the reflective sensing device.

Each of the emitters 305, 310, 315, and 320 include short paths 355 and long paths 360 to each of the other detectors 325, 330, 335, and 340. For example, emitter 320 has a short path 355 to detector 325, a short path to detector 340, a long path to detector 330 and a long path to detector 335. The long paths and the short paths may provide a mapping of arterial or venous blood flow for pulse oximetry. Further, the long paths and the short paths may provide an array of potentially differing perspectives of the arterial or venous blood flow signals for pulse oximetry. Each of the detectors may be capable of receiving or detecting light from each of the emitters 305, 310, 315, and 320 and each wavelength of each of the emitters. For example, detectors 325, 330, 335, and 340 may each be capable of sensing green light, infrared light, and red light.

FIG. 3 depicts four emitters and four detectors, which may provide sixteen different optical paths between emitters and detectors. Although FIG. 3 and other examples discussed herein may use four emitters and four detectors, any number of emitter and detectors may be used as appropriate. For example, as shown in other embodiments herein, three emitters and three detectors may be used in the reflective sensing device and may provide nine optical paths or up to nine optical paths between the emitters and detectors. In some examples, the higher the number of paths, the less sensitive the measurements may be to erroneous data. With a greater number of measurements, it may be easier to verify data with redundant or consistent measurements and may also be easier to identify erroneous data by comparing outlying measurements or inconsistent data.

Additionally, the greater the distance between emitters and detectors, the greater amount of wrist tissue may be imaged and/or optically probed with the measurements. One or more of the path signals may be used to image and/or optically probe the wrist tissue, thus the number of emitters and detectors and the distance between emitters and detectors may be appropriately chosen to image and/or probe as much of the wrist tissue as possible for the corresponding size of the wearable device. In some examples, the higher the number of emitters and detectors, the greater the number of optical paths over which to probe and/or take measurements for imaging the wrist tissue. However, the number of emitters and detectors may also be considered when optimizing the appearance of the wearable device and accounting for battery life of the wearable device.

Although the reflective sensing device may have multiple emitters and detectors there may be a predetermined sequence for turning the emitters and detectors on and off. In some examples, emitter 305 may be turned on, but the emitter 305 may turn on the single green light emitter 305a. Continuing this example, the adjacent detectors, detector 325 and detector 330, may be turned on to detect a returned amount of the green emitted light. In other examples, emitter 305 may be turned on and the infrared light emitter 305b and the red light emitter 305c may be turned on to emit light and detectors 325, 330, 335, and 340 may be all turned on to detect a returned amount of the infrared and red light. Some embodiments may turn on emitters 305 and 315, or may turn on emitters 315 and 320, or may turn on all the emitters at once. The order in which the emitters may be sequentially turned on may be predetermined or may be random. In some examples, all the emitters and detectors may be turned on at the same time.

As previously discussed, the detectors 325, 330, 335, and 340 may sense an amount of returned light (e.g., reflected light and/or backscattered light) that has passed through the arterial blood of the user. The detectors may include additional associated circuitry which may be configured to process the detected light measurements into signals and may provide these electrical signals to a processor. In some examples, the detected light measurements may be from each detector individually, or may be aggregate measurements derived from two or more detectors. The processor may be configured to receive the signals (or indicators, or outputs) from one or more of the detectors. In some examples, the processor may be configured to receive signals from one or more of the emitters. Additionally, the processor may be further configured to determine a blood oxygenation level using at least a subset of the received signals (or indicators or outputs) and in some cases the received or detected light. In some examples, the processor may be configured to receive the signals (or indicators or outputs) representing a detected range of red light and infrared light wavelengths from at least a first detector and a second detector, for example detectors 325 and 330. The processor may then determine a blood oxygenation level using a subset of the signals (or indicators or outputs) representing the received range of red light wavelengths and the received range of infrared light wavelengths.

In some examples, the processor may be configured to select which of the detector measurements to use and may select a subset of the received detector measurements. Additionally or alternatively, the process may be configured to select for use the signals and/or measurements associated with one or more of the emitters. The processor may be configured to use various factors to select the subset of measurements such as determining erroneous outlying measurements or being able to detect false reading measurements that may appear to be useful measurements, but may not comply with the assumptions that were made for taking the measurements. The processor may utilize data received from multiple optical paths or channels and weigh various features to identify useful data—e.g., by analyzing multiple views and/or regions of the wrist tissue, obtained by acquiring measurements over multiple optical paths. In other examples, the processor may use all of the data received from the detectors. Further, in some cases, the measurement and/or signals received from the detectors may be weak signals. By choosing which of the detector measurements to use, the processor may select sufficiently strong signals, or in some examples may select multiple signals (e.g., amounts of detected light) to sum together. Additionally, the emitters and detectors may be located father away from one another because the detector signals may be added together.

In the example of FIG. 3, an amount of the green light emitted by emitter 305a may be detected by the closest detectors, detector 325 and detector 330. As previously discussed and as illustrated in FIG. 3, the green light emitters 305a, 310a, 315a, and 320a may be located the farthest away from the central portion of the wearable device back cover. The green light emitters may be less sensitive to the location because the green light may be detected by the closest detectors. Additionally, by locating the green light emitters close to the detectors, the battery life and power savings of the wearable device may benefit. Generally, green light may be used for heart rate detection and monitoring when incorporated into a wearable device. In some embodiments, the detected green light may also be used to differentiate good detector readings from erroneous detector readings (i.e., the amounts of detected green light may be used to determine a subset of red light and infrared light measurements (or indicators) used to determine a blood oxygenation level).

Figure 4:
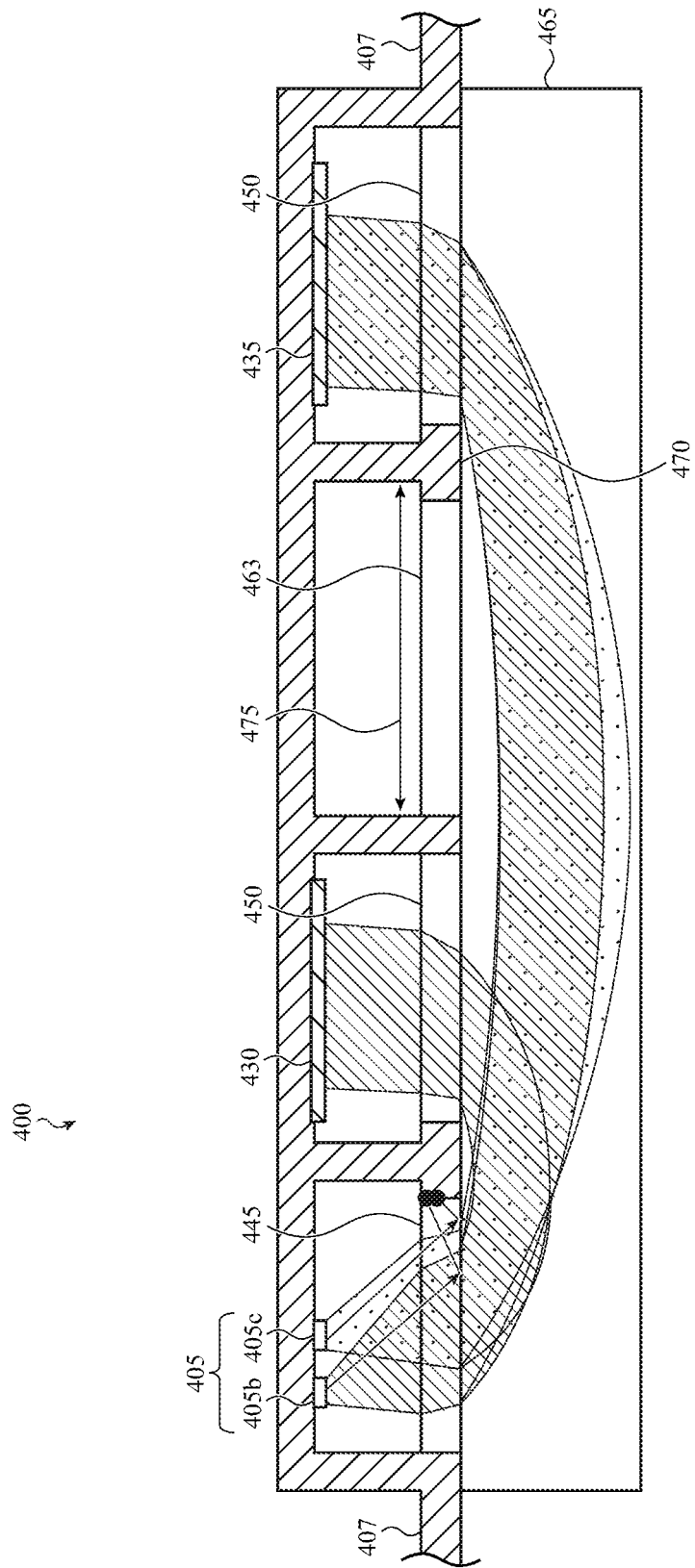
FIG. 4 illustrates an example layout of emitters and detectors.

FIG. 4 illustrates an example layout 400 of emitters and detectors. In some examples, the layout 400 of emitters and detectors may be incorporated into some aspects of the wearable device 100 as described with reference to FIGS. 1A-3. In the example of FIG. 4, the layout 400 of emitters and detectors may be included in the wearable device to provide physiological and/or biometric measurements of the user wearing the wearable device as discussed with respect to FIGS. 1A-3.

By way of example and for purposes of description, the layout 400 of emitters and detectors may be located on the back or skin-facing side of the wearable device 100 as discussed with reference to FIGS. 1A and 1B. The layout 400 of emitters and detectors may be protected by a back or skin-facing cover with windows or apertures which is discussed in further detail herein.

As illustrated in FIG. 4, the layout 400 may include a window 445 for the emitter 405 and windows 450 for the near detector 430 and the far detector 435. The optional window 463 may be a window over the central portion of the back cover 407 of the wearable device. The windows may be disposed in openings 475 in the back cover 407 and may sit on or abut ledges 470. Alternatively, some or all of the windows may be integral with the back cover 407 and defined by an absence of an optical mask (e.g., an ink (an optically opaque ink), film, coating, or surface treatment) on other portions of the back cover 407. For example, the optical mask may be on first portions (e.g., non-window portions) of the back cover 407, and absent from second portions of the back cover 407. In some cases, and by way of example, the window 445 for the emitter 405 may be defined by the absence of an optical mask (e.g., the ink, film, coating, or surface treatment) that surrounds the window 445, and the windows 450 for the near detector 430 and the far detector 435 may sit on or abut ledges 470. The openings in the back cover and the ledges are discussed in further detail herein. The back cover 407 and/or windows 445, 450, 463 may be formed of sapphire, glass, plastic, or other materials.

In some cases, the emitter 405, the near detector 430, and the far detector 435 may be mounted to a printed circuit board (PCB), and the PCB may be attached to the back cover 407 by one or more components that form a set of optical barriers (or walls) between the PCB and the back cover 407. In these cases, the back cover 507, in combination with the PCB and one or more components that form the set of optical barriers (or walls), may define different cavities in which the emitter 405, the near detector 430, and the far detector 435 are separately housed.

The windows of FIG. 4 may form a surface with the back cover and the back cover 407 may be adjacent to the wrist tissue 465. The emitter 405 may include an infrared light emitter 405b and a red light emitter 405c. The light from the infrared light emitter 405b and the red light emitter 405c may pass into the tissue 465. The light reflected from the arterial blood flood and/or that has passed through a user's arterial blood and/or tissue 465 may pass through the windows 450 to the near detector 430 and the far detector 435. As previously discussed, the near detector 430 and the far detector 435 may be configured to receive or detect light from any of the emitters and to receive or detect reflected green light, infrared light, and/or red light. The ledges 470 may serve at least partially as optical isolators between the emitter window(s) and the detector windows which will be discussed in further detail herein.

As depicted in FIG. 4, the emitter 405c may emit red light through the window 445. The red light may pass through the window 445 to the tissue 465. The red light may reflect off a first area of tissue and back through the window 450 to be received or detected by the near detector 430. Additionally, the red light may reflect off a second area of tissue and back through the window 450 to be received or detected by the far detector 435. Further illustrated in FIG. 4, the red light reflected off the first area of tissue may not penetrate as deep into the tissue as the red light reflected off the second area of tissue. By placing the emitter and the detector farther away from one another, the light may penetrate different depths into the tissue, thus providing a more thorough image mapping and/or probing of the wrist tissue. Red light from emitter 405b may also enter the window 445 at such an angle that it may not be able to pass through the window due to total internal reflection (TIR). As shown in FIG. 4, the red light may reflect off of the external surface of the window towards the skin and reflect back into the window. The reflected red light may not be detected by the detector 430 since the reflected red light may be absorbed by the barrier or ledge 470 separating window 445 from window 450. The barrier or ledge 470 may isolate light emitted directly from the emitter from being detected by the detector, thus preventing undesirable internal crosstalk.

The light emitted from infrared light emitter 405b may pass through window 445 and enter the skin 465. The infrared light may reflect off of the arterial vessels in the skin 465 and may pass through window 450. The infrared light may then be sensed by the far detector 435. In the example of FIG. 4, the infrared light may not be received by the near detector 430. As illustrated, some of the emitted infrared light may not pass through the window 445 due to the angle at which it is emitted and may instead be reflected off of the window due to TIR. This infrared light may reflect off of the window and back into the window. The emitted infrared light reflected off the window and not the tissue, may not be detected by the detector 430 as it may be blocked by the optical barrier or ledge 470. The optical barrier or ledge 470 may isolate light which may be emitted at certain angles within the window 445 and at least partially reduce or prevent internal crosstalk and may prevent light emitted by the emitter from being sensed directly by a sensor without passing through the user's tissue first. In some examples of FIG. 4, infrared light may be reflected, scattered and/or backscattered out of the tissue and into the near detector 430. Although not depicted in FIG. 4, red light emitted by red light emitter 405c may be reflected, scattered and/or backscattered out of the tissue and into either one of the detectors 430 and detector 435. Similarly, infrared light emitted by infrared light emitter 405b may be reflected, scattered and/or backscattered out of the tissue and into either one of the detectors 430 and detector 435. The method of forming these windows with optical barriers via ledges 470 and other methods of providing optical isolation within the windows are discussed in further detail herein.

Figure 5A:
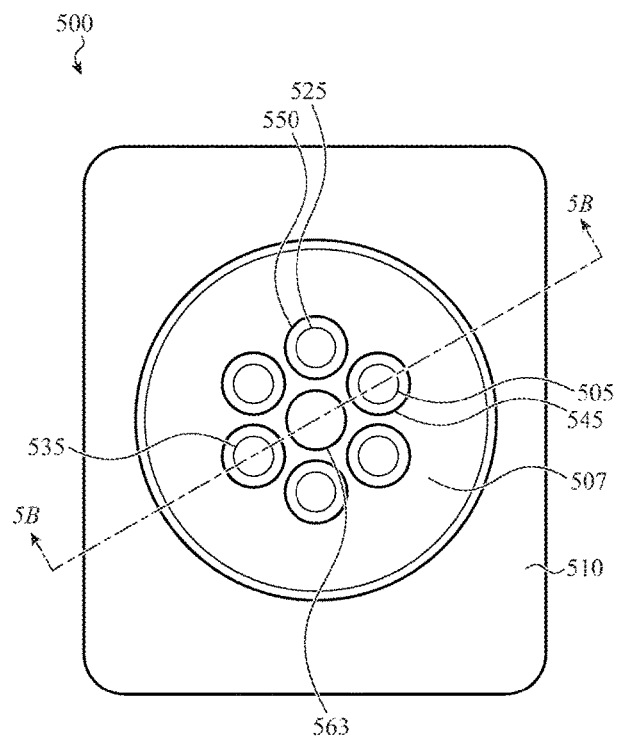
FIG. 5A illustrates an example of a back side of a wearable device.

Each of FIGS. 5A-5D show a different view of the back cover and/or back side of the wearable device as previously described with reference to FIGS. 1A-4. FIG. 5A illustrates an example 500 of a back side 510 of a wearable device. In some examples, the back side 510 may be incorporated into some aspects of the wearable device 100 as described with reference to FIGS. 1A-4. In the example of FIG. 5, the back side 510 may be incorporated in the wearable device to provide physiological and/or biometric measurements of the user wearing the wearable device as discussed with respect to FIGS. 1A-4. As illustrated in FIG. 5A, the back side 510 of the wearable device may include the back cover 507. The back cover 507 may have six inset windows disposed about a central portion (or central window 563) of the back cover 507. The windows 545 may provide apertures through which emitters may emit light and the windows 550 may provide apertures through which detectors may detect light reflected off of a user's arterial blood flow and/or may detect backscattered light that has passed through a user's arterial blood. The windows may be inset into openings that extend through the back cover 507. Although the back cover 507 may include inset windows, the windows may form a smooth surface with the back cover 507.

Figure 5B:
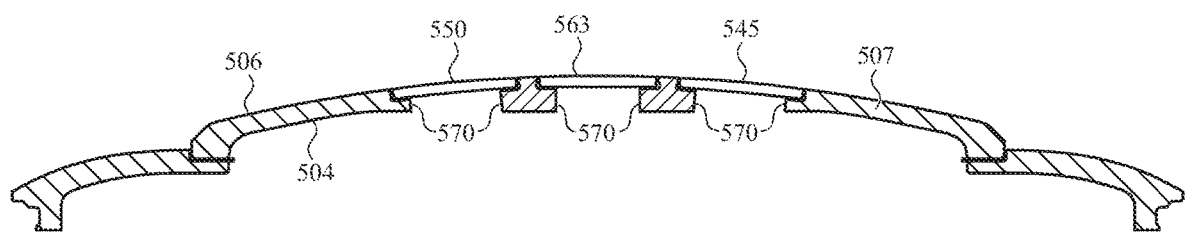
FIG. 5B illustrates an example of a back cover of a wearable device from the side view.

FIG. 5B illustrates an example elevation of a back cover 507 of a wearable device. In some examples, the back cover 507 may be incorporated into some aspects of the wearable device 100 as described with reference to FIGS. 1A-5A. In the example of FIG. 5B, the back cover 507 may be incorporated in the wearable device to provide physiological and/or biometric measurements of the user wearing the wearable device as discussed with respect to FIGS. 1A-5A.

Figure 5C:
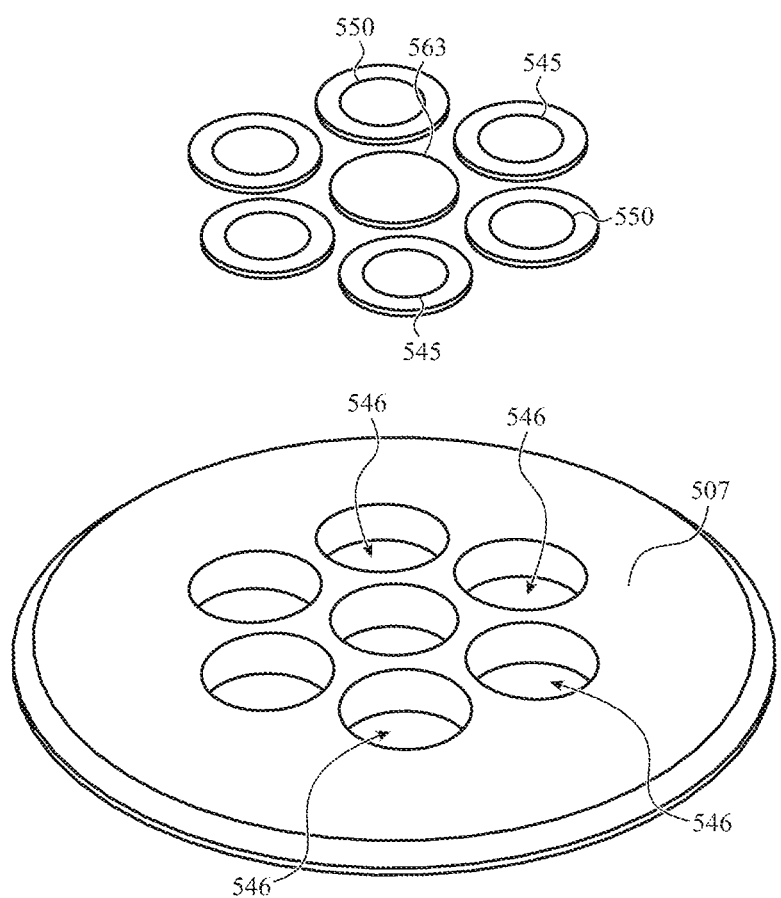
FIG. 5C illustrates an example of a back cover of a wearable device.

As illustrated in FIG. 5B, the side view may be a cross section toward the middle of the back side of the wearable device as depicted in FIG. 5A. The back cover 507 may include six peripheral windows disposed around a central portion of the back cover 507. In some embodiments, the central portion may include an optional center window. As previously mentioned, any appropriate number of windows may be used and six windows are used for explanatory and discussion purposes only. Window 545 may provide an aperture through which an emitter may emit light and window 550 may provide an aperture through which a detector may detect light reflected off of and/or backscattered from the user's tissue. Window 563 (as illustrated in FIGS. 5A, 5B, and 5C) may be in a central portion (or center) of the wearable device and is optional. In some examples, window 563 may be employed to enable an optical sensor to detect whether the wearable device is contacting a user's skin, or to monitor a user's heart rate, or for other purposes. For example, an IR LED or other emitter may in some cases emit IR light through a central window, and an IR detector may detect a portion of the emitted IR light that is returned through the central window after reflecting or scattering off of a user. The returned portion of the emitted IR light may be used to determine whether the back cover is or is not adjacent a user's wrist (or is no longer adjacent a user's wrist), or the returned portion of the emitted IR light may be analyzed to determine the user's heart rate. In some cases, a central window, and/or optical sensing through a central window, may be incorporated into any of the device embodiments described herein.

In FIG. 5B the back cover 507 may have an internal surface 504 which may be internal to the wearable device and an external surface 506 which may be external to the wearable device. Further, the back cover 507 may include a substrate which may define at least part of the internal surface 504 and the external surface 506 of the wearable device. The external surface 506 may be the surface which may come into contact with the skin of the user wearing the wearable device. The back cover 507 or skin-facing cover may have openings which may extend through the back cover, for example the openings may extend through the internal surface and the external surface of the back cover 507. The back cover 507 may also include a set of ledges 570 which may border the openings as illustrated in FIG. 5B. In some examples, the ledges 570 may be stepped ledges, the ledges may extend entirely around the openings as shown and discussed with respect to FIGS. 5A-5D, or the ledges may be positioned at select angular extents about the openings, or other appropriate shapes or gradients as discussed herein. The windows may be disposed in the openings and may abut the ledges 570. The windows may be bonded in place to the back cover 507 and also to the ledges, which may secure the windows into place such that the windows may not be displaced or become tilted in the openings of the back cover 507. The windows may be bonded using any appropriate method such as an adhesive, melting, and so forth. In some examples, the entire back cover 507 may be optically opaque or the entire back cover 507 may be optically transparent. The back cover 507 may be optically opaque or transparent to the light emitted and/or detected or received by the wearable device.

In some examples of FIG. 5B, the ledges 570 may extend into the openings of the back cover 507. The ledges may extend into the openings to provide an edge on which the windows may rest. The ledges may provide a protruding edge on which the windows may sit. The ledges may ensure that the windows do not fall through the back cover and into the internal part of the wearable device. These ledges may be positioned adjacent to or near the internal surface of the back cover. Alternatively, the ledges may be adjacent to or near the external surface of the back cover so that the windows may be inserted from the outside or external surface of the back cover.

In some examples, the back cover 507 with the ledges may be an optically opaque material and the windows may be optically transparent. As used herein, optically opaque may not block 100% of all light across all wavelengths, and may instead block a targeted wavelength of light which may be appropriately attenuated. In this example, the ledges may provide at least some optical isolation for the detectors so that stray light from the emitters may not be received at the detectors. Within a certain range of angles, light leaving the emitters may reflect off of the windows back toward the detector instead of passing through the window and into the tissue. Without optical isolation, this light that reflects off of the windows may be received by the detectors and may provide an erroneous measurement. With optical isolation, the light that reflects off of the windows and back towards the detector may be prevented from reaching the detector by the optically opaque ledge that optically isolates the detector. In some examples, the windows over the detectors may have optical barriers, while in other examples, the windows over the emitters may have optical barriers, and in further examples, the windows over both the emitters and the detectors may have optical barriers. In some examples, the optical barrier may be formed by coating the sides of the openings and/or the sides of the windows (e.g., surrounding the openings or windows) with an optically opaque ink or other material that is optically opaque to the emitted and detected light. Additionally or alternatively, the optical barrier may be formed by one or more of an ink, film, coating, or surface treatment disposed between a window and its respective opening (or ledge). The ink, film, coating, or surface treatment may be formed on, or applied to, the window or the opening (or ledge) before the window is abutted to and attached to the opening (or ledge).

In some examples, the detectors may detect a specific range of wavelengths, such as IR wavelengths. In this example, the optical barrier or optically opaque material may block the specific range of wavelengths that the detector detects (so that the emitted wavelengths are not detected by the detector without first passing through the back cover 507); or the optical barrier may block all wavelengths of light; or the optical barrier may block at least the range of IR wavelengths as well as some range on both sides of the IR wavelengths.

In some embodiments, the back cover 507 and/or windows 545, 550, 563 may be formed of sapphire, glass, plastic, or other materials. Although the windows may be optically transparent, in some examples the distance between the ledges may at least partially determine the size of the apertures through which light may pass. As previously discussed, the windows may abut the ledges and the ledges may be optical barriers between the emitters and the detectors. The ledges may have protruding edges for the windows to sit upon, thus the distance between the inner side of the ledges may be smaller than the openings and/or the windows. Accordingly, the area through which light may pass may be smaller than the openings in the back cover and instead may be the inner distance between the ledges.

FIG. 5C illustrates an example of a back cover 507 of a wearable device. In some examples, the back cover 507 may be incorporated into some aspects of the wearable device 100 as described with reference to FIGS. 1A-5B. In the example of FIG. 5C, the back cover 507 may be incorporated in the wearable device to provide physiological and/or biometric measurements of the user wearing the wearable device as discussed with respect to FIGS. 1A-5B.

As illustrated in FIG. 5C, the perspective view may be an example of the back cover 507 of the wearable device as depicted in FIGS. 5A and 5B. The back cover 507 may include six windows 545, 550 disposed around a central portion (or optional central window 563) of the back cover 507. As previously mentioned, any appropriate number of windows (such as eight windows) may be used and six windows are used in this figure for explanatory and discussion purposes only. Windows 545 may provide an aperture through which an emitter may emit light and windows 550 may provide an aperture through which a detector may detect light reflected off of and/or backscattered from the user's tissue. Window 563 may be in the central portion (or center) of the wearable device. The back cover 507 and/or windows 545, 550, 563 may be formed of sapphire, glass, plastic, or other materials.

Figure 5D:
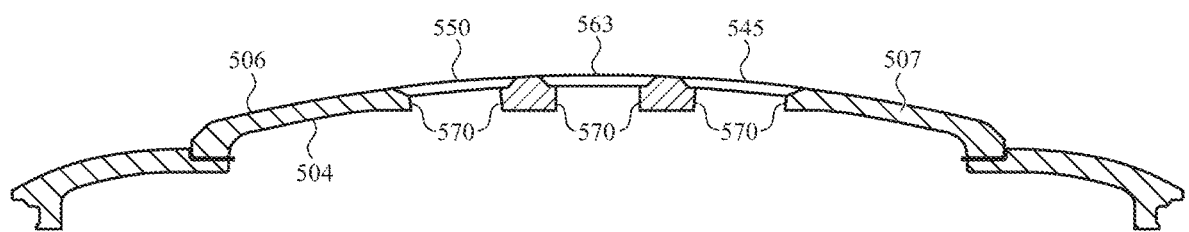
FIG. 5D illustrates an example of a back cover of a wearable device from the side view.

The back cover 507 may include openings 546 that extend through the back cover. The openings 546 may include ledges which may be stepped, tapered, cupped, or any other appropriate profile to at least partially support the window in the back cover 507. In some examples, the ledges may be tapered, and the taper may be a shallow taper as illustrated in FIG. 5D. In still other examples, the taper may extend through the openings of the back cover 507. In this example, the window may be the depth of the back cover 507.

In some examples, the ledges 570 may determine the size of the aperture through which light may pass or be detected. The windows 545, 550 may rest on or at least be partially supported by the ledges 570 and the windows 545, 550 may be optically transparent so that light may pass through or be detected through the windows 545, 550. In some examples, the back cover 507 may be optically opaque.

In other examples, the back cover 507 may be optically translucent or transparent and the windows 545, 550 may be optically translucent or transparent. In this example, the optically transparent back cover 507 may include ledges 570, but the ledges 570 may be coated with an optically opaque material such as ink to provide light blocking or optical isolation between the emitters and the detectors. Additionally, the ledges 570 may be optically transparent and the edges of the windows 545, 550 may be coated with an optically opaque ink. In yet another embodiment, both the ledges 570 and the edges of the windows 545, 550 may be coated with an optically opaque ink to provide the optical barrier between the emitters and the detectors.

FIG. 5D illustrates an example side view of a back cover 507 of a wearable device. In some examples, the back cover 507 may be incorporated into some aspects of the wearable device 100 as described with reference to FIGS. 1A-5B. In the example of FIG. 5D, the back cover 507 may be incorporated in the wearable device to provide physiological and/or biometric measurements of the user wearing the wearable device as discussed with respect to FIGS. 1A-5C.

As illustrated in FIG. 5D, the view may be an example of the back cover 507 of the wearable device as depicted in FIG. 5C. Similar to FIG. 5B, FIG. 5D illustrates the ledges 570 on which the windows 545, 550 may rest. The ledges 570 of FIG. 5D may be tapered as opposed to the stepped ledges of FIG. 5B.

Figure 6A:
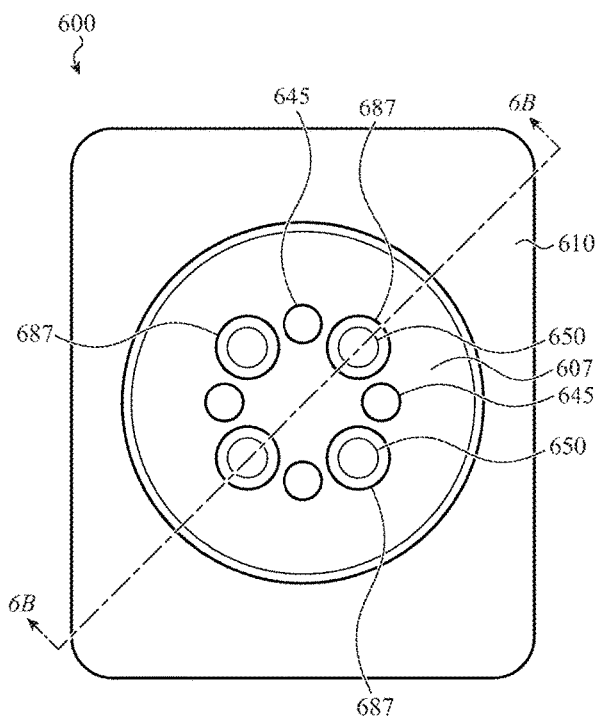
FIG. 6A illustrates an example of a back side of a wearable device.
Figure 6B:
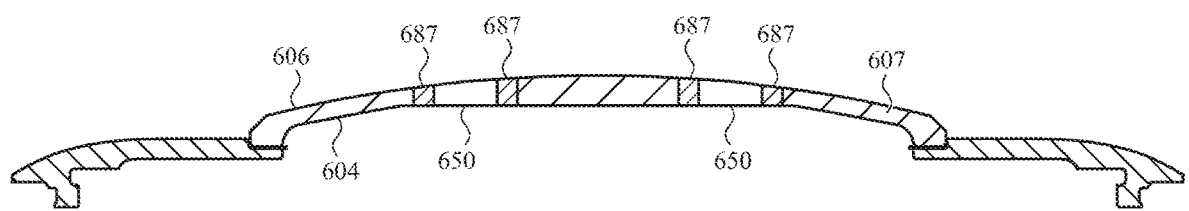
FIG. 6B illustrates an example of a back cover of a wearable device from the side view.
Figure 6C:
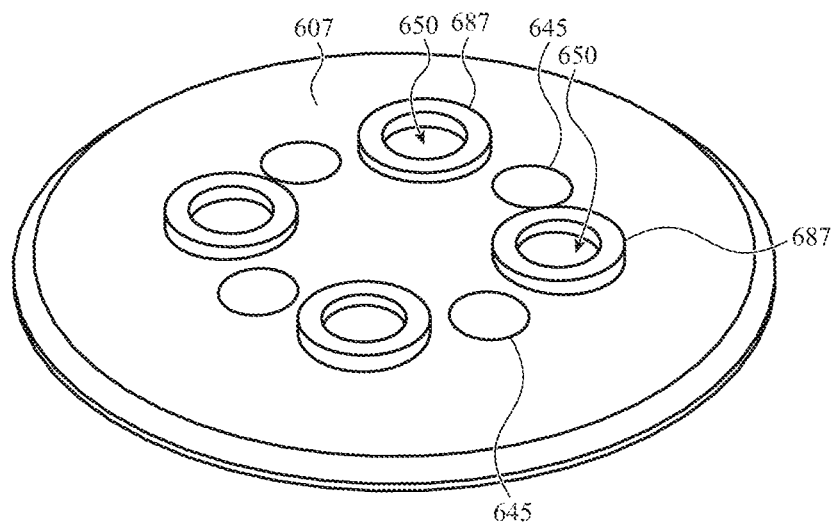
FIG. 6C illustrates an example of a back cover of a wearable device.

Each of FIGS. 6A-6C show a different view of the back cover on the back side of the wearable device as previously described in FIGS. 1A-5D. FIG. 6A illustrates an example 600 of a back side 610 of a wearable device. In some examples, the back side 610 may be incorporated into some aspects of the wearable device 100 as described with reference to FIGS. 1A-5D. In the example of FIG. 6A, the back side 610 may be incorporated in the wearable device to provide physiological and/or biometric measurements of the user wearing the wearable device as discussed with respect to FIGS. 1A-5D.

As illustrated in FIG. 6A, the back side 610 of the wearable device may include the back cover 607. The back cover 607 may have four to eight inset windows which may provide sixteen optical sensing paths or channels. The windows 650 may provide apertures through which detectors may detect light reflected off of a user's arterial blood flow and/or may detect backscattered light that has passed through a user's arterial blood. The back cover and/or windows may be formed of sapphire, glass, plastic, or other materials. The windows 650 (and in some cases, the windows 645) shown in FIG. 6A may be inset into openings that extend through the back cover 607. Although the back cover 607 may include inset windows, the windows may form a smooth exterior surface with the back cover 607. As depicted in FIG. 6A, four of the eight windows (e.g., windows 650) may have an optically opaque or opaque material 687 around the perimeter of the window, which may determine the size of the aperture through which light may pass. The optically opaque or black material around the perimeter of the window may be an optical barrier for all light or an optical barrier for at least the range of wavelengths emitted and/or received by the emitters and the detectors of the wearable device. The other four windows (e.g., windows 645) may be integral portions of a monolithic back cover structure (i.e., the windows 645 may not be inset windows) and may be defined by an optical mask (e.g., an ink, film, coating, or surface treatment) on the back cover 607. For example, the ink film, coating, or surface treatment may be on first portions of the back cover 607 and absent on second portions of the back cover 607.

FIG. 6B illustrates an example of a back cover 607 of a wearable device from the side view. In some examples, the back cover 607 may be incorporated into some aspects of the wearable device 100 as described with reference to FIGS. 1A-6A. In the example of FIG. 6B, the back cover 607 may be incorporated in the wearable device to provide physiological and/or biometric measurements of the user wearing the wearable device as discussed with respect to FIGS. 1A-6A.

As illustrated in FIG. 6B, the side view may be a cross section of the back side of the wearable device as depicted in FIG. 6A. As depicted in FIG. 6A, the back cover 607 may include eight windows. As previously mentioned, any appropriate number of windows may be used and eight windows are used for explanatory and discussion purposes only. Each of windows 645 may provide an aperture through which an emitter may emit light and each of windows 650 may provide an aperture through which a detector may detect light reflected off of and/or backscattered from the user's tissue. By way of example, the cross section shown in FIG. 6B shows the windows 650 inset into, and extending through, the back cover 607. As previously discussed, the windows 645 may be integral portions of the back cover 607 and may not be inset. As shown in FIGS. 6A and 6B, there may be no window in the central portion (or center) of the wearable device. However, in some embodiments, there may be a central window as shown in FIG. 5A.

In FIG. 6B the back cover 607 may have an internal surface 604 which may be internal to the wearable device and an external surface 606 which may be external to the wearable device. The back cover 607 may include a substrate which may at least partially define the internal surface 604 and the external surface 606 of the wearable device. The external surface 606 may be the surface which may come into contact with the skin of the user wearing the wearable device. Similar to FIG. 5B, in FIG. 6B, the back cover 607 or skin-facing cover may have openings which may extend through the back cover. For example, the openings may extend through the internal surface 604 and the external surface 606 of the back cover 607. In this ledge-less example of FIG. 6B, glass or sapphire optically transparent frits 687 may include a central portion that is hollow (for example, similar to a hollow tube) and may be approximately cylindrical in shape. The frits 687 may be inserted into the openings of the back cover 607, and the frits may border the perimeter of the openings as illustrated in FIG. 6B and be melted or bonded to the back cover 607. Windows 650 may be disposed in the center of the fits 687 and the windows may be bonded in place and to the back cover 607. In some examples, windows 650 may provide an aperture though which light reflected off of and/or backscattered light passing through a user's arterial blood flow may be detected. By melting or bonding the fits and the windows 650 to the back cover, this may secure the frits and windows into place such that the windows may not be displaced or become tilted in the openings of the back cover 607. Additionally, the internal surface 604 and external surface 606 of the back cover 607 may be ground or polished to provide a back cover with smooth surfaces. Further, although the frits and windows may be depicted as round, the fits and the windows may be any appropriate shape. In some examples, the inner diameter of the frit may be any shape so long as the frit functions as an optical barrier and blocks the emitter to detector light path.

In some examples of FIG. 6B, the frits may be optically opaque. Either the frit material itself may be optically opaque, or the frits may be coated with an optically opaque material such as an optically opaque ink or a color neutral ink which may not distinguish between infrared and red light. The frits may be inserted into the opening, and the frits may have frit openings similar to a ring. Because the frits are similar to a ring with a hollow central opening, the inner diameter of the frit may provide an aperture through which light may still be detected. In some embodiments, the frit may be a glass frit (e.g., a black glass frit) which may be centered in the opening of the back cover 607. The black glass frit may form an optical bond with the sapphire opening after melting or bonding and then both sides of the back cover may be polished to achieve a smooth surface. In this embodiment, the masking of the emitter and/or detector may be determined by the shape of the ink and or the frit. The frits may be any shape so long as the frit blocks the emitter to detector optical path.

In some examples, the back cover 607 may be an optically transparent material and the windows may also be optically transparent. The optically opaque frits may provide at least some optical isolation for the detectors so that stray emitter light may not be received at the detectors. Within a certain range of angles, light leaving the emitters may reflect off of the windows back toward the detector instead of passing through the window and into the tissue. Without optical isolation, this light that reflects off of the windows may be received by the detectors and may provide an erroneous measurement. With optical isolation, the light that reflects off of the windows and back towards the detector may be prevented from reaching the detector by the optically opaque frit that optically isolates the detector.

Similar to FIGS. 5A-5C, the size of the apertures through which light may pass to reach a detector may be at least partially determined by the inner diameter of the frit and/or the ink on the perimeter of the frit. In FIG. 6B, the inner diameter of the frit and/or the ink on the inner diameter of the frit may be the optical barrier between the emitters and the detectors. Accordingly, the area through which light may pass may be smaller than the openings in the back cover and instead may be the inner diameter of the frits.

FIG. 6C illustrates an example of a back cover 607 of a wearable device. In some examples, the back cover 607 may be incorporated into some aspects of the wearable device 100 as described with reference to FIGS. 1A-6B. In the example of FIG. 6C, the back cover 607 may be incorporated in the wearable device to provide physiological and/or biometric measurements of the user wearing the wearable device as discussed with respect to FIGS. 1A-6B.

As illustrated in FIG. 6C, the isometric view may be an example of the back cover 607 of the wearable device as depicted in FIGS. 6A and 6B. The back cover 607 may include four to eight windows. Windows 645 may provide an aperture through which an emitter may emit light, and in some cases may be integral with the back cover 607 and defined by the absence of an optical mask (e.g., an ink (an optically opaque ink), film, coating, or surface treatment) on other portions of the back cover 607. For example, the optical mask may be on first portions of the back cover 607, and absent from second portions of the back cover 607. Windows 650 may provide an aperture through which a detector may detect light reflected off of and/or backscattered from the user's tissue and may be inset into the back cover 607. In FIG. 6C, there may be no separately provided window in the central portion (or center) of the wearable device. However, the back cover 607, or a portion thereof, may in some cases be optically transparent to a range of electromagnetic radiation wavelengths that is emitted and/or received through the central portion of the back cover.

In FIG. 6C, the back cover 607 may include openings for the windows 650 that extend through the back cover. The openings may be ring shaped fits with an opening in the central portion and the frits may be inserted into the openings and may function as a sleeve that fits within the opening of the back cover. The inner diameter opening of the fits or the ink coated on the frits may determine the size of the aperture through which light may pass or be detected. Although the term frit may be used herein, a frit may be understood to be a hollow sleeve, ring, and/or tube shaped component or hollow cylindrical element regardless of material composition.

The windows 650 may be disposed in the frit center opening and may be optically transparent so that light may pass or be detected through the windows. The frits 687 may function as optical barriers between the emitters and detectors and may minimize or prevent internal crosstalk. Using optical isolation, any emitter light that reflects off of the windows and back towards the detector may be prevented from reaching the detector by the optically opaque frit that optically isolates the detector.

Figure 7:
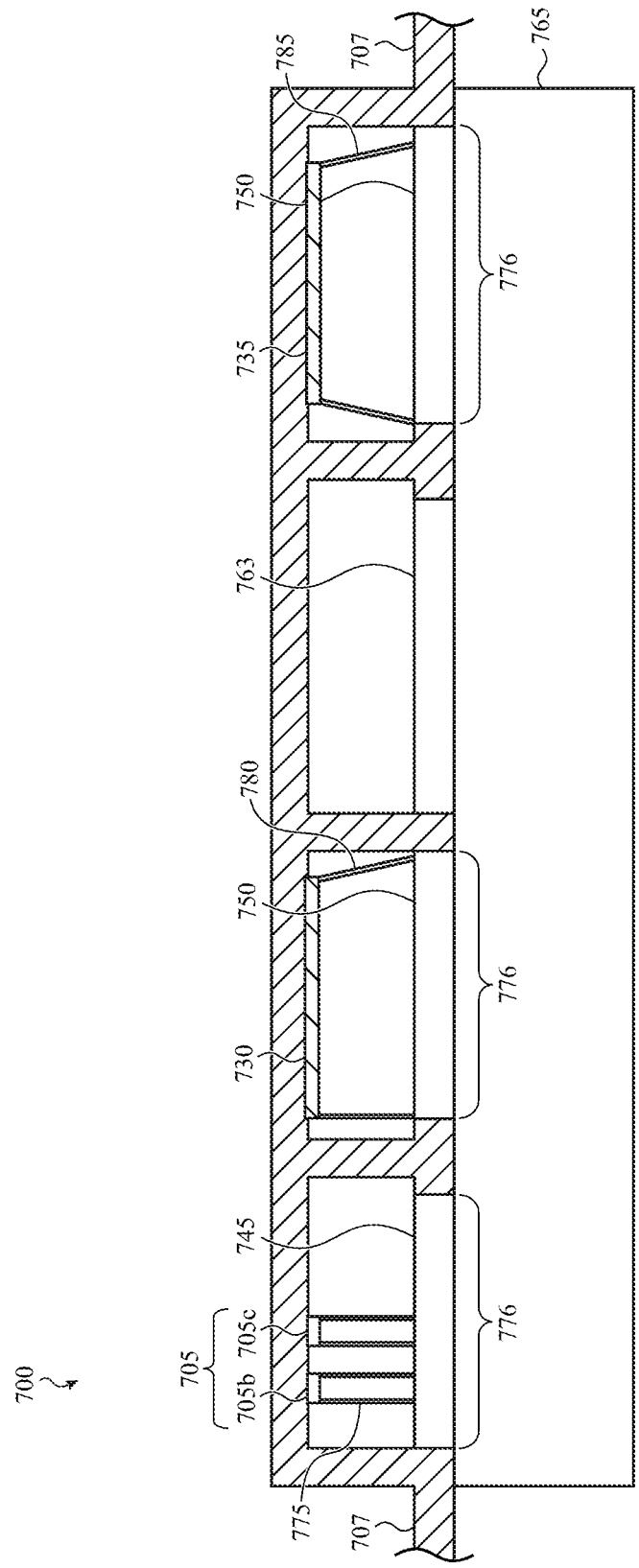
FIG. 7 illustrates an example of a back cover, emitters, detectors, and waveguides of a wearable device from the side view.

FIG. 7 illustrates an example 700 of a back cover, emitters, detectors, and waveguides of a wearable device from the side view. In some examples, the back cover 707 may be incorporated in the wearable device to provide physiological and/or biometric measurements of the user wearing the wearable device as discussed with respect to FIGS. 1A-6C.

As illustrated in FIG. 7, the side view may be a cross section of the wearable device as depicted in FIG. 5A. The back cover 707 may include six windows, but the side view of FIG. 7 shows an emitter window, and two detector windows. In FIG. 7, the emitter and detectors may be protected by a back or skin-facing cover with windows or apertures. Window 745 provides an aperture through which the emitter may emit light and window 750 may provide an aperture through which a detector may detect light reflected off of and/or backscattered from the user's tissue. As illustrated in FIG. 7, the window 745 for the emitter 705 and windows 750 for the near detector 730 and the far detector 735. The optional window 763 may be a window over the central portion of the back cover 707 of the wearable device. The windows may be disposed in openings 776 in the back cover 707 and the back cover 707 may be an optically transparent or opaque back cover. The openings in the back cover may extend through the interior surface and the exterior surface of the back cover. Alternatively, some or all of the windows may be integral with the back cover 707 and defined by an absence of an optical mask (e.g., an ink (an optically opaque ink), film, coating, or surface treatment) on other portions of the back cover 707. For example, the optical mask may be on first portions (non-window portions) of the back cover 707, and absent from second portions of the back cover 707. In some cases, and by way of example, the window 745 for the emitter 705 may be defined by the absence of an optical mask (e.g., the ink, film, coating, or surface treatment) that surrounds the window 745, and the windows 750 for the near detector 730 and the far detector 735 may be disposed in openings 776 in the back cover 707. The back cover 707 and/or windows 745, 750, 763 may be formed of sapphire, glass, plastic, or other materials.

In some cases, the emitter 705, the near detector 730, and the far detector 735 may be mounted to a PCB, and the PCB may be attached to the back cover 707 by one or more components that form a set of optical barriers (or walls) between the PCB and the back cover 707. In these cases, the back cover 707, in combination with the PCB and one or more components that form the set of optical barriers (or walls), may define different cavities in which the emitter 705, the near detector 730, and the far detector 735 are separately housed.

In FIG. 7, the optical path for emitted light, between the emitter 705 and the window 745, may be determined by an emitter waveguide 775. The emitter waveguide 775 may guide the emitted light from the emitter to the window. In some examples, the light may be received in a first end of the waveguide such that the light internally reflects off the walls of the waveguide. The light may exit a second end of the waveguide and through the window and/or into the tissue of the user wearing the device. The emitter waveguide 775 may be internally reflective at or around the wavelength of light being generated or emitted. Further, the emitter waveguide 775 may guide the emitted light via total internal reflection in the waveguide 775 and to the emitter window 745. Additionally, the emitter waveguide 775 may be configured to transmit the light from the emitter to the wrist of the user wearing the wearable device.

As depicted in FIG. 7, there may be an emitter waveguide 775 for each of the emitters which may emit different light wavelengths, but in some embodiments, there may be one waveguide configured to receive emitted light from more than one emitter. For example, the emitter waveguide 775 may be configured to receive all of the emitted green light, the emitted red light, and the emitted infrared light, and guide the light to the emitter window 745. In other examples, the emitter waveguide 775 may extend through the back cover of the wearable device and the back cover may not include windows. In this example, the emitters may emit the light through a housing of a reflective sensing device.

Also illustrated in FIG. 7, the optical path for light reflected off of and/or backscattered light that has passed through arterial or venous blood flow of the wrist, between the near detector 730 and the detector window 750, may be determined by the near waveguide 780. The near waveguide 780 may guide the reflected light from the window to the near detector 730. The near waveguide 780 may be internally reflective at or around the wavelength of light being received at the near detector 730. In some examples, the near detector 730 may be internally reflective at or around the range of red light, infrared light, and/or green light wavelengths. Further, the near waveguide 780 may guide the reflected light via total internal reflection in the waveguide 780, from the window and to the near detector 730. In some examples, the near waveguide 780 may extend through the back cover of the wearable device and the back cover may not include windows.

Similarly, the optical path between the far detector 735 and the detector window 750 may be determined by the far waveguide 785. The far waveguide 785 may guide the reflected light from the detector window 750 to the far detector 735. The far waveguide 785 may be internally reflective at or around the wavelength of light being received at the far detector 735. In some examples, the far detector 735 may be internally reflective at or around the range of red light, infrared light, and/or green light wavelengths. Further, the far waveguide 785 may guide the reflected light via total internal reflection in the far waveguide 785, from the window and to the far detector 735.

In some examples, the near and far detectors 730, 735 may include additional associated circuitry which may be configured to process the detected light measurements into signals and may provide these electrical signals to a processor. The processor may be configured to receive the signals from one or more of the detectors. Additionally, the processor may be further configured to determine a blood oxygenation level using at least a subset of the received signals and in some cases received detected light. In some examples, the processor may be configured to receive the signals representing a detected range of red light and infrared light wavelengths from a far detector 735 and a near detector 730. The processor may then determine a blood oxygenation level using a subset of the signals representing the received range of red light wavelengths and the received range of infrared light wavelengths The waveguides of FIG. 7 may be formed of sapphire, plastic, glass, or any other appropriate material. In some examples, the waveguides may be fiber optic waveguides which may be similar to a plastic rod with internally reflective material that reflects light at or around a range of green light wavelengths, a range of red light wavelengths, and a range of infrared light wavelengths. In other examples, the waveguides may be similar to hollow tubes and internally reflective of light at or around a range of green light wavelengths, a range of red light wavelengths, and a range of infrared light wavelengths. The waveguides of FIG. 7 may be optically coupled with the emitters and detectors via butt coupling, one or more prisms, one or more lenses, and/or any other appropriate method, or any combination thereof. Additionally, the waveguides of FIG. 7, may be any appropriate shape such as a sheet or film, cable, straight, tapered, any combination thereof, and so forth. In some examples, the far waveguide 785 may extend through the back cover of the wearable device and the back cover may not include windows.

In other examples of FIG. 7, the back cover may have openings, but no optically transparent windows. Instead, the waveguide may fill the opening in the back cover. In this example, the waveguide may directly receive the reflected and/or backscattered light that has passed through the arterial and venous blood flow of the person. The waveguides may be plastic, glass, hardened glass, a solid rod, a hollow tube, or any other appropriate configuration or material or any combination thereof. In some examples, the waveguides may be fiber optic waveguides which may be similar to a solid plastic rod with internally solid reflective material that reflects light at or around green light wavelengths, red light wavelengths, and infrared light wavelengths. In other examples, the fiber optic waveguides may be similar to a hollow plastic tube in which the light may propagate through air, but the internal perimeter wall of the hollow plastic tube may be a reflective material that reflects ranges of light at or around green light wavelengths, red light wavelengths, and infrared light wavelengths.

The emitter waveguide 775, the near waveguide 780 and the far waveguide 785 may be optical waveguides, including but not limited to, fiber optic, single-mode, step index, gradient index, light guides, planar, films, any combination thereof, and so forth. In some examples, the emitter waveguide 775, the near waveguide 780 and the far waveguide 785 may be different types of waveguides from one another. The waveguides may be inserted into holes or openings machined into the back cover 707. The emitter waveguide 775 may ensure that the emitted light transmits toward the tissue and not directly toward the near detector 730 or the far detector 735. In some examples, each of the individual emitters of emitter 705 may have a corresponding waveguide. For example, the red light emitter may have a waveguide, the infrared light emitter may have a waveguide, and the green light emitter may have a waveguide. In additional examples, the near detector 730 and the far detector 735 may not have waveguides associated with the detectors as discussed with respect to FIGS. 5A-5D and 6A-6C.

In some examples, the emitter waveguide 775, the near waveguide 780 and the far waveguide 785 may have an internal core which is reflective of the wavelengths around green light, infrared light, and red light. Further, the core of the waveguide may be minimally absorbing around these wavelengths so that the greatest amount of the emitted light may be transmitted to the wrist tissue of the user wearing the wearable device and not absorbed by the waveguide. Additionally, the waveguide internal core may be minimally absorbing around these wavelengths so that the light reflected off of and/or backscattered from the wrist tissue may be detected by the near detector 730 and the far detector 735.

FIGS. 8A-8D illustrate various layouts 800, 805, 806, and 809 for the back cover of the wearable device. The windows of the back cover 807 shown in any of the layouts 800 described with reference to any of FIGS. 8A-8D may in some examples be configured so that a first set of windows may be configured to transmit emitted light to the wrist of the user and a second set of windows may be configured to detect light reflected off of the arterial flow of the user and/or backscattered light that has passed through arterial blood. Additionally, the layouts 800 may be used in any of the examples described with respect to FIGS. 1A-7. The back covers and/or windows in each of the layouts may be formed of sapphire, glass, plastic, or other materials.

Figure 8A:
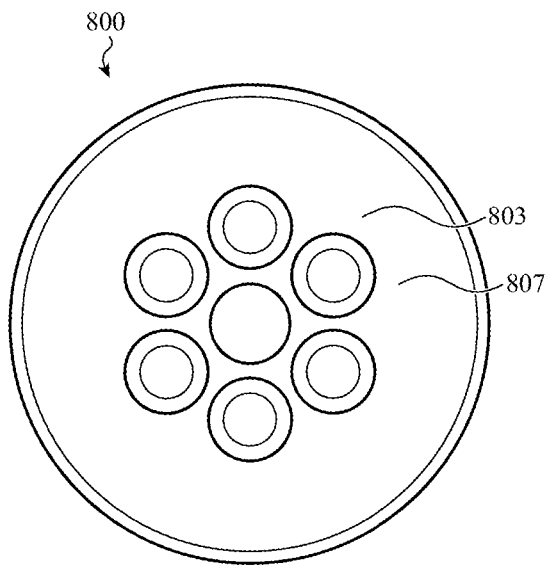
FIG. 8A illustrates an example of a back cover of a wearable device.

FIG. 8A illustrates an example 800 of a back cover of a wearable device. In some examples, the back cover 807 may be incorporated in the wearable device to provide physiological and/or biometric measurements of the user wearing the wearable device as discussed with respect to FIGS. 1A-7. As illustrated in FIG. 8A, the back cover 807 may include six windows disposed around a central portion (or central window) as described herein. The windows of the back cover 807 in FIG. 8A may be circularly shaped and may provide nine optical paths between the emitters and detectors and may be used with either the ledge embodiments discussed with respect to FIGS. 5A-5D, the frit embodiments discussed with respect to FIGS. 6A-6C, or the waveguide embodiments discussed with respect to FIG. 7. In FIG. 8A, the emitting area may be defined by the inner diameter of the frit, or the distance between the inner edges of the ledges as discussed herein. Although the windows may be larger, the aperture through which light may pass may be determined by the optical barriers between the emitters and the detectors. In other examples of FIG. 8A, the windows of the back cover 807 in FIG. 8A may provide up to nine optical paths between the emitters and detectors.

Figure 8B:
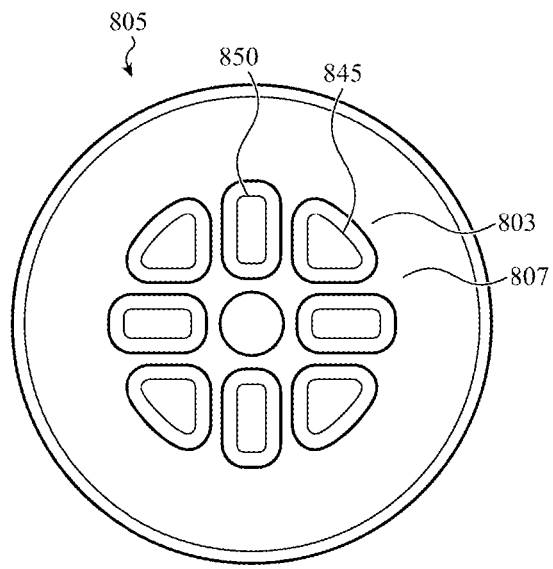
FIG. 8B illustrates an example of a back cover of a wearable device.

FIG. 8B illustrates an example 803 of a back cover of a wearable device. In some examples, the back cover 807 may be incorporated in the wearable device to provide physiological and/or biometric measurements of the user wearing the wearable device as discussed with respect to FIGS. 1A-8A. As illustrated in FIG. 8B, the back cover 807 may include eight windows as described in detail herein. The windows of the back cover 807 in FIG. 8B may be rectangular and triangular shapes and may provide sixteen optical paths between the emitters and detectors, and in some examples, may provide up to sixteen optical paths between the emitters and detectors. The example of FIG. 8B may be used with either the ledge embodiments discussed with respect to FIGS. 5A-5D, the frit embodiments discussed with respect to FIGS. 6A-6C, or the waveguide embodiments discussed with respect to FIG. 7. In FIG. 8B, the shapes of the windows and apertures may be implemented to maximize the use of as much of the surface area of the back cover 807 as possible. Further, in FIG. 8B, the green light emitter may be located in the inner diameter of the triangular shapes and the red light emitter and the infrared light emitter may be located in the corners of the triangular shapes.

Figure 8C:
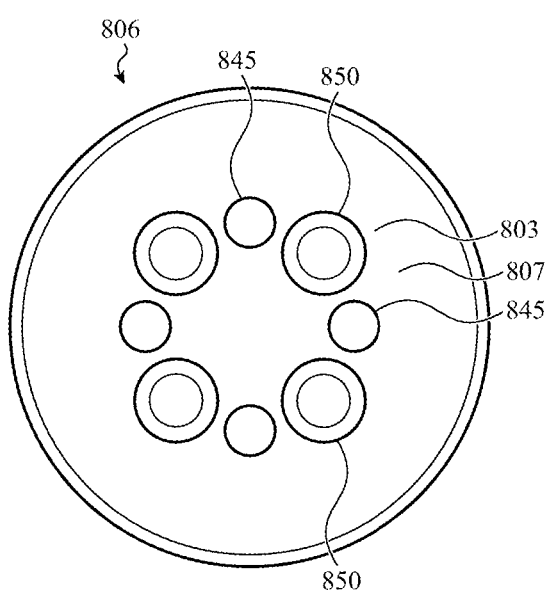
FIG. 8C illustrates an example of a back cover of a wearable device.

FIG. 8C illustrates an example 806 of a back cover of a wearable device. In some examples, the back cover 807 may be incorporated in the wearable device to provide physiological and/or biometric measurements of the user wearing the wearable device as discussed with respect to FIGS. 1A-8B. As illustrated in FIG. 8C, the back cover 807 may include eight windows as described in detail herein. The windows of the back cover 807 in FIG. 8C may be circular, and may provide sixteen optical paths between emitters and detectors. The example of FIG. 8C may be used with either the ledge embodiments discussed with respect to FIGS. 5A-5D, the frit embodiments discussed with respect to FIGS. 6A-6C, or the waveguide embodiments discussed with respect to FIG. 7.

In FIG. 8C, the windows 850 through which light may be detected after reflecting off of the wrist arterial flow may include optical barriers (e.g., ledges, inks, films, coatings, surface treatments, or frits, as described with reference to FIGS. 1B-7) that extend through the back cover 807, around (or defining) the inner diameters of the windows. Although all of the apertures may be the same size in FIG. 8C, the windows 845 through which emitted light may pass may not have optical barriers that extend through the back cover 807 (but may). Instead, the windows 845 may be integral with the back cover 807 (i.e., the windows 845 may not be inset windows) and have diameters defined by an absence of an optical mask (e.g., an ink (an optically opaque ink), film, coating, or surface treatment) applied to other portions of the inner or outer surface of the back cover 807. For example, the optical mask may be on first portions (e.g., non-window portions) of the back cover 807, and absent from second portions of the back cover 807. The optical mask may define a size of an aperture over each emitter, but may not block light from being redirected within the back cover 807. However, emitted light that is redirected within the back cover 807, without exiting the back cover 807, may be blocked from reaching a detector by the optical barriers that extend through the back cover 807 and around detector windows. The optical barriers may be formed by one or more of an ink, film, coating, surface treatment, or frit disposed between a window and its respective opening, which in some cases may be entirely or partially surrounded by a stepped or tapered ledge. In the cases of an ink, film, coating, or surface treatment, the ink, film, coating, or surface treatment may be formed on, or applied to, the window or the opening (or ledge) before the window is abutted to and attached to the opening (or ledge). The windows 850 may be larger than the windows 845, but the apertures of windows 850 and the apertures of the windows 850 may be the same size. In some examples, the windows 850 may include an optical barrier, for example the ledges or the frits, which may result in the apertures being smaller than the windows 850.

Figure 8D:
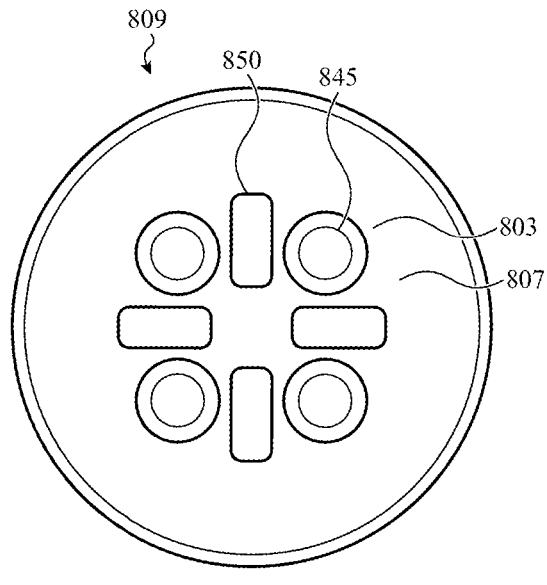
FIG. 8D illustrates an example of a back cover of a wearable device.

FIG. 8D illustrates an example 809 of a back cover of a wearable device. In some examples, the back cover 807 may be incorporated in the wearable device to provide physiological and/or biometric measurements of the user wearing the wearable device as discussed with respect to FIGS. 1A-8C. As illustrated in FIG. 8D, the back cover 807 may include eight windows as described in detail herein. The windows of the back cover 807 in FIG. 8D may be rectangular and circular shapes and may provide sixteen optical paths between the emitters and detectors. The example of FIG. 8D may be used with either the ledge embodiments discussed with respect to FIGS. 5A-5D, the frit embodiments discussed with respect to FIGS. 6A-6C, or the waveguide embodiments discussed with respect to FIG. 7. In FIG. 8D, the shapes of the windows and apertures may be implemented to maximize the use of as much of the surface area of the back cover 807 as possible. Further, in FIG. 8D, the emitters may be linear shaped to use as much of the aperture opening as possible. With the implementation of the linear shaped emitters, the emitters may emit stronger or more intense light for transmission into the wrist tissue of the user. In other examples, the windows of the back cover 807 in FIG. 8D may provide up to sixteen optical paths between the emitters and detectors.

Figure 9A:
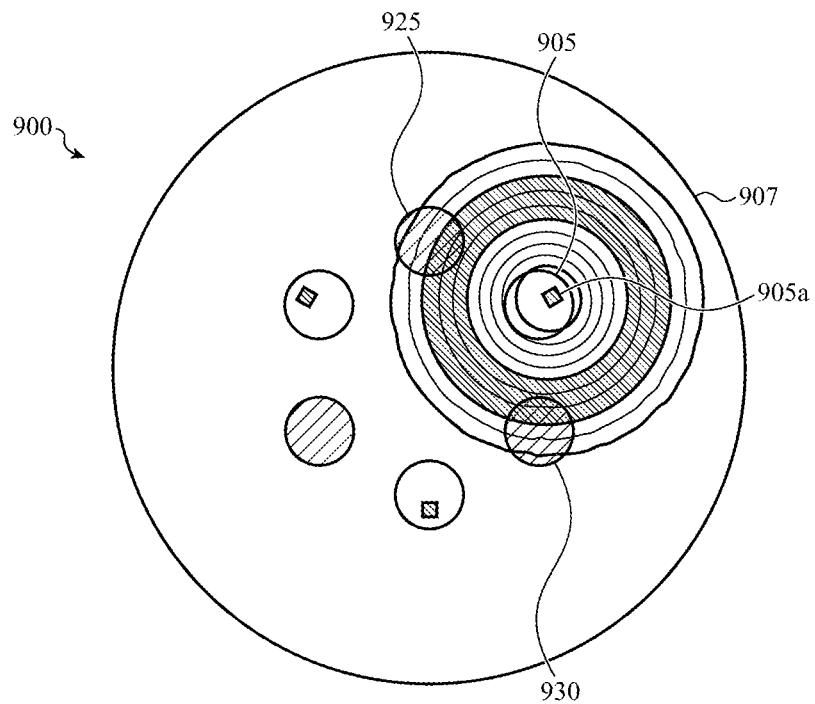
FIG. 9A illustrates a layout of a back cover of a wearable device.
Figure 9B:
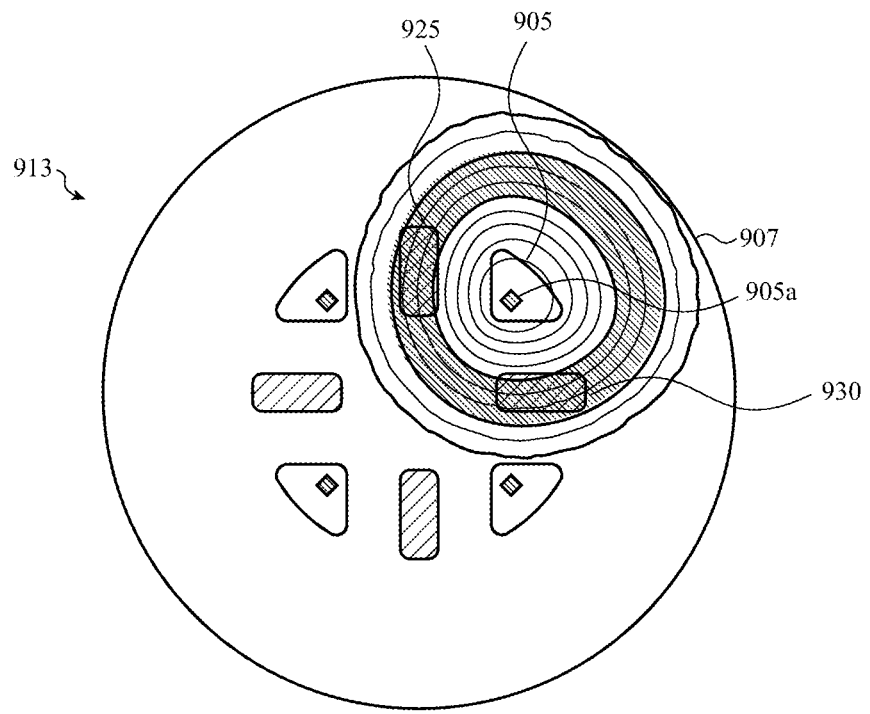
FIG. 9B illustrates a layout of a back cover of a wearable device.

FIGS. 9A and 9B illustrate various layouts for the back cover of the wearable device. The windows of the back cover shown in the layouts 900 and 913 described with reference to both FIGS. 9 and 10 may in some examples be configured so that windows may be configured to transmit emitted light to the wrist of the user and may be further configured to detect light reflected off of the arterial flow of the user and/or backscattered light that has passed through arterial blood. Additionally, the layouts may be used in any of the examples described with respect to FIGS. 1A-8D.

FIG. 9A illustrates a layout 900 of a back cover of a wearable device. In some examples, the back cover 907 may be incorporated in the wearable device to provide physiological and/or biometric measurements of the user wearing the wearable device as discussed with respect to FIGS. 1A-8D. As illustrated in FIG. 9A, the back cover 907 may include six windows disposed around a central portion (or central window) of the back cover 907, similar to FIG. 8A, and may provide nine optical paths between the emitters and detectors. In other examples of FIG. 9A, the back cover 907 may include six windows similar to FIG. 8A and may provide up to nine optical paths between the emitters and detectors. The windows of the back cover 907 in FIG. 9A may be circular shapes. The windows may alternatively have alternate shapes or sizes, and may be more or fewer in number.

As illustrated in FIG. 9A, the green light emitter 905a of emitter 905 may emit green light. The green light may be transmitted from the green light emitter and may reflect off of the arterial blood flow, and may be detected by detectors 925 and 930. FIG. 9A depicts that the light reflected off of the blood vessels may be stronger or a higher intensity in some locations and weaker or a lower intensity in other locations. Due to the circular layout and circular shape of the windows and apertures, only part of the reflected green light may line up with the detectors. Although the signal may provide useful information, it may be desirable for as much reflected light as possible to be detected by the detector, as opposed to only part of the reflected light being detected on the periphery of the detector.

FIG. 9B illustrates a layout 913 of a back cover of a wearable device. In some examples, the back cover 907 may be incorporated in the wearable device to provide physiological and/or biometric measurements of the user wearing the wearable device as discussed with respect to FIGS. 1A-8D. As illustrated in FIG. 9B, the back cover 907 may include eight windows similar to the layout of FIG. 8B and may provide sixteen optical paths between the emitters and detectors. In other examples of FIG. 9B, the back cover 907 may include eight windows and may provide up to sixteen optical paths between the emitters and detectors. The windows of the back cover 907 in FIG. 9B may be triangular and rectangular shapes.

As illustrated in FIG. 9B, the green light emitter 905a of emitter 905 may emit green light and as previously discussed may be located in the inner part of the triangular window and aperture. The green light may be transmitted from the green light emitter and may reflect off of the arterial blood flow, and may be detected by detectors 925 and 930. FIG. 9B depicts that the light reflected off of the blood vessels may be stronger or a higher intensity in some locations and weaker or a lower intensity in other locations. Due to the circular layout and the rectangular shape of the windows and apertures for the detectors 925 and 930, the reflected green light may "line up" or overlap with most to all of the detecting area of the detectors 925 and 930. The detectors 925 and 930 may receive or detect as much reflected light as possible, as opposed to detecting reflected light in the periphery of the detector as described with respect to FIG. 9A.

The described layouts and configurations of the wearable device in FIG. 1A-9B have been for explanatory purposes. In alternative embodiments, the described embodiments may include a different combination or configuration of components, or may perform additional or alternative functions. The layouts and configurations described herein may be used as part of an electronic device, such as, in a watch, a biometric sensor, or in any other appropriate device.

In various embodiments, components or inks are indicated to be "opaque" or "optically opaque." A component or ink is typically optically opaque to an emitted or received electromagnetic radiation wavelength of a component over which it is positioned, or to a range of emitted or received electromagnetic radiation wavelengths, and may thus block the wavelength(s). In some cases, the components or inks may also be optically opaque to, or block, other or all electromagnetic radiation wavelengths. In some cases, a component or ink may also be optically opaque to visible light for aesthetic reasons and/or other reasons.

In various embodiments, components or inks are indicated to be "transparent" or "optically transparent." A component or ink may only be optically transparent to an emitted or received electromagnetic radiation wavelength of a component over which it is positioned, or to a range of emitted or received electromagnetic radiation wavelengths, and may thus pass the wavelength(s). In some cases, the components or inks may also be optically transparent to, or pass, other or all electromagnetic radiation wavelengths.

In some embodiments, the inks described herein may alternatively be or include one or more of a coating, surface treatment, and so on. In some embodiments, multiple inks, coatings, or surface treatments may be combined to provide one or more bands of optical blocking and/or optical transparency.

In some embodiments, opaque, selectively opaque, and/or selectively transparent components, inks, coatings, surface treatments, or the like may be used to reduce unwanted optical crosstalk between an emitter and a receiver, or between different optical paths.

Figure 10:
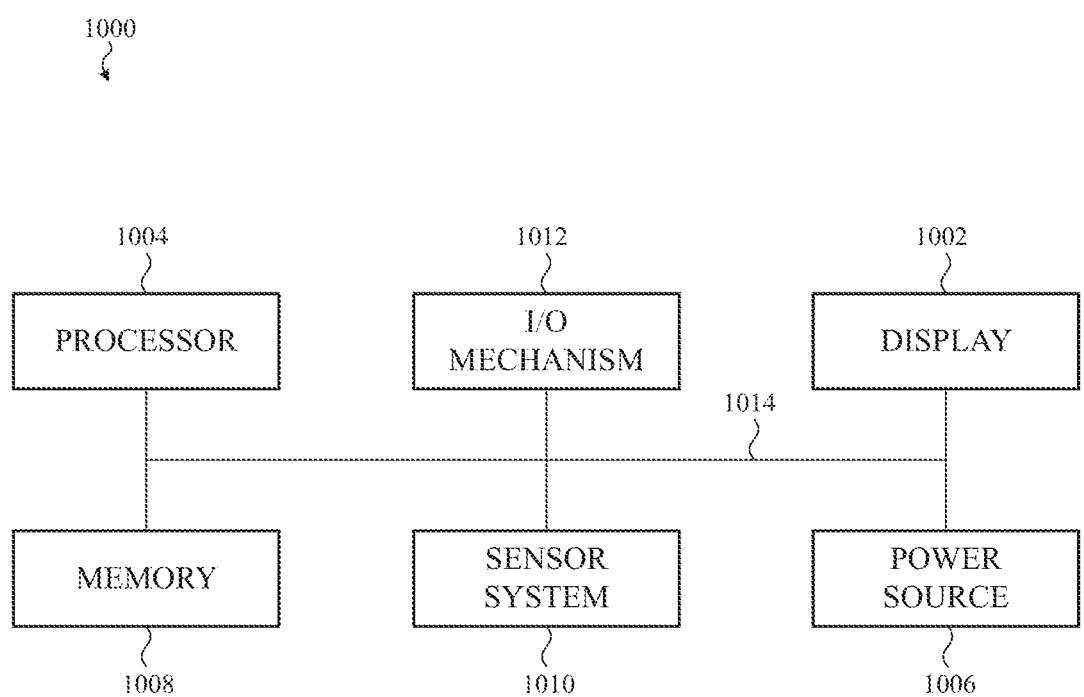
FIG. 10 illustrates a sample electrical block diagram of an electronic device.

FIG. 10 illustrates a sample electrical block diagram of an electronic device 1000, and which may be the electronic device described with reference to FIGS. 1A-9B. The electronic device 1000 may include a display 1002 (e.g., a light-emitting display on the front side of a wearable device), a processor 1004, a power source 1006, a memory 1008 or storage device, a sensor system 1010, and an input/output (I/O) mechanism 1012 (e.g., an input/output device and/or input/output port). The processor 1004 may control some or all of the operations of the electronic device 1000. The processor 1004 may communicate, either directly or indirectly, with substantially all of the components of the electronic device 1000. For example, a system bus or other communication mechanism 1014 may provide communication between the processor 1004, the power source 1006, the memory 1008, the sensor system 1010, and/or the I/O mechanism 1012.

The processor 1004 may be implemented as any electronic device capable of processing, receiving, or transmitting data or instructions. For example, the processor 1004 may be a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitably configured computing element or elements.

It should be noted that the components of the electronic device 1000 may be controlled by multiple processors. For example, select components of the electronic device 1000 may be controlled by a first processor and other components of the electronic device 1000 may be controlled by a second processor, where the first and second processors may or may not be in communication with each other. In some embodiments, the processor 1004 may include any of the processors and/or may be capable of any of the processing steps described herein.

The power source 1006 may be implemented with any device capable of providing energy to the electronic device 1000. For example, the power source 1006 may be one or more batteries or rechargeable batteries. Additionally or alternatively, the power source 1006 may be a power connector or power cord that connects the electronic device 1000 to another power source, such as a wall outlet.

The memory 1008 may store electronic data that may be used by the electronic device 1000. For example, the memory 1008 may store electrical data or content such as, for example, audio and video files, documents and applications, device settings and user preferences, timing signals, control signals, data structures or databases, image data, biometric data, or focus settings. The memory 1008 may be configured as any type of memory. By way of example only, the memory 1008 may be implemented as random access memory, read-only memory, Flash memory, removable memory, other types of storage elements, or combinations of such devices.

The electronic device 1000 may also include a sensor system 1010, which in turn includes one or more sensors positioned substantially anywhere on the electronic device 1000, for example the back side of a wearable device. The sensor(s) may be configured to sense substantially any type of characteristic, such as but not limited to, pressure, electromagnetic radiation (light), touch, heat, movement, relative motion, biometric data, and so on. For example, the sensor(s) may include a heat sensor, a position sensor, a light or optical sensor, an accelerometer, a pressure transducer, a gyroscope, a magnetometer, a health monitoring sensor, and so on. Additionally, the one or more sensors may utilize any suitable sensing technology, including, but not limited to, capacitive, ultrasonic, resistive, optical, ultrasound, piezoelectric, and thermal sensing technology.

The I/O mechanism 1012 may transmit and/or receive data from a user or another electronic device. An I/O device may include a display, a touch sensing input surface such as a track pad, one or more buttons (e.g., a graphical user interface "home" button), one or more cameras, one or more emitters and/or detectors (e.g., the wearable device with biometric sensors described with reference to FIGS. 1A-9B as described herein), one or more microphones or speakers, one or more ports such as a microphone port, and/or a keyboard. Additionally or alternatively, an I/O device or port may transmit electronic signals via a communications network, such as a wireless and/or wired network connection. Examples of wireless and wired network connections include, but are not limited to, cellular, Wi-Fi, Bluetooth, IR, and Ethernet connections.

The foregoing description, for purposes of explanation, uses specific nomenclature to provide a thorough understanding of the described embodiments. However, it will be apparent to one skilled in the art, after reading this description, that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art, after reading this description, that many modifications and variations are possible in view of the above teachings, and that various features of the example embodiments may be combined for a particular application.

The present disclosure recognizes that personal information data, including the biometric data acquired using the presently described technology, can be used to the benefit of users. For example, the use of biometric authentication data can be used for convenient access to device features without the use of passwords. In other examples, user biometric data is collected for providing users with feedback about their health or fitness levels. Further, other uses for personal information data, including biometric data that benefit the user are also contemplated by the present disclosure.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure, including the use of data encryption and security methods that meets or exceeds industry or government standards. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates embodiments in which users selectively block the use of, or access to, personal information data, including biometric data. That is, the present disclosure contemplates that hardware and/or software elements can be provided to prevent or block access to such personal information data. For example, in the case of biometric authentication methods, the present technology can be configured to allow users to optionally bypass biometric authentication steps by providing secure information such as passwords, personal identification numbers (PINS), touch gestures, or other authentication methods, alone or in combination, known to those of skill in the art. In another example, users can select to remove, disable, or restrict access to certain health-related applications collecting users' personal health or fitness data.

What is claimed is:

1. A wearable device, comprising:
a housing;
a display viewable through a front side of the housing;
a skin-facing cover on a back side of the housing and formed from an optically transparent material, and having:
an interior surface;
an exterior surface; and
a set of ledges bordering a set of openings, the set of openings extending through the skin-facing cover from the interior surface to the exterior surface;
a set of windows disposed in the set of openings and abutting the set of ledges;
a set of optical barriers positioned between the set of windows and the set of ledges; and
a set of photodetectors disposed within the housing and configured to receive light through the set of windows.

2. The wearable device of claim 1, wherein:
the skin-facing cover is formed of sapphire; and
each window in the set of windows is formed of sapphire.

3. The wearable device of claim 1, wherein the set of ledges are stepped ledges.

4. The wearable device of claim 3, further comprising:
a set of red light emitters;
a set of infrared light emitters; and
a set of green light emitters; wherein,
the set of windows is a first set of windows;
the skin-facing cover further includes a second set of windows;
a red light emitter in the set of red light emitters, an infrared light emitter in the set of infrared light emitters, and a green light emitter in the set of green light emitters is disposed under each window in the second set of windows; and
windows in the first set of windows and the second set of windows are interspersed in a ring around a central portion of the skin-facing cover.

5. The wearable device of claim 1, wherein:
each ledge of the set of ledges extends into an opening along the interior surface of the skin-facing cover; and
each window of the set of windows is positioned on a respective ledge of the set of ledges.

6. The wearable device of claim 5, wherein each window in the set of windows comprises an outer surface that is flush with the exterior surface of the skin-facing cover.

7. The wearable device of claim 1, wherein the set of ledges each comprise an optically opaque material.

8. The wearable device of claim 7, wherein the optically opaque material blocks at least a range of red light wavelengths and a range of infrared light wavelengths detectable by the set of photodetectors.

9. A wearable device, comprising:
a housing;
a display viewable through a front side of the housing;
a cover on a back side of the housing and formed from an optically transparent material, and having:
an interior surface;
an exterior surface;
a set of openings extending through the cover from the interior surface to the exterior surface; and
a set of ledges each bordering an opening of the set of openings,
a first set of windows each positioned in an opening the set of openings and abutting a respective ledge of the set of ledges;
a set of emitters positioned within the housing and configured to emit light through the first set of windows;
a second set of windows each positioned in an opening of the set of openings and abutting a respective ledge of the set of ledges; and
a set of photodetectors positioned within the housing and configured to receive light through the second set of windows.

10. The wearable device of claim 9, further comprising optical isolation material positioned between the second set of windows and a respective opening of the set of openings.

11. The wearable device of claim 10, wherein the optical isolation material is configured to block wavelengths of light that are emitted by one or more emitters of the set of emitters.

12. The wearable device of claim 10, wherein emitters of the set of emitters are configured to emit red light wavelengths, infrared light wavelengths or a combination thereof.

13. The wearable device of claim 10, wherein:
a first subset of the set of photodetectors are configured to detect a first wavelength of light;
a second subset of the set of photodetectors are configured to detect a second wavelength of light;
the cover comprises a first optical isolation material positioned between windows associated with the first subset of the set of photodetectors, the first optical isolation material configured to block the first wavelength of light; and
the cover comprises a second optical isolation material positioned between windows associated with the second subset of the set of photodetectors, the second optical isolation material configured to block the second wavelength of light.

14. The wearable device of claim 10, wherein:
each ledge of the set of ledges extends into the opening along the interior surface of the cover; and
each window of the first and second sets of windows is positioned on a respective ledge of the set of ledges.

15. The wearable device of claim 14, wherein the each ledge of the set of ledges comprises a tapered profile.

16. A wearable device, comprising:
a housing;
a display positioned at least partially within an opening of a front side of the housing;
a cover on a back side of the housing, and formed from an optically transparent material, and having:
   an interior surface;
   an exterior surface; and
   a set of openings extending through the cover from the interior surface to the exterior surface, each opening in the set of openings defining a ledge;
optical isolation material positioned around a periphery of each opening in the set of openings;
a set of windows comprising windows each positioned in an opening of the set of openings and abutting a respective ledge; and
a set of photodetectors disposed within the housing and configured to receive light through the set of windows.

17. The wearable device of claim 16, further comprising one or more light emitters positioned in the housing, wherein:
   the one or more light emitters are configured to emit light through one or more first openings of the set of openings; and
   the set of photodetectors are configured to receive light through one or more second openings of the set of openings.

18. The wearable device of claim 17, wherein the one or more light emitters comprise:
   a first light emitter positioned within a first opening of the set of openings and configured to emit light at a first wavelength; and
   a second light emitter positioned within the first opening and configured to emit light at a second wavelength, different from the first wavelength.

19. The wearable device of claim 16, wherein:
each respective ledge comprises a stepped feature; and
each window of the set of windows is positioned on the stepped feature of a respective ledge.

20. The wearable device of claim 16, wherein:
each respective ledge comprises a tapered surface; and
each window of the set of windows defines a tapered surface that contacts the respective tapered surface of a respective opening.

* * * * *